(12) United States Patent
Valery et al.

(10) Patent No.: US 9,180,387 B2
(45) Date of Patent: Nov. 10, 2015

(54) METHOD AND DEVICE FOR SEPARATING FRACTIONS OF A MIXTURE

(75) Inventors: Eric Valery, Pulnoy (FR); Olivier Ludemann-Hombourger, Pompey (FR)

(73) Assignee: NOVASEP PROCESS, Pompey (FR)

( * ) Notice: Subject to any disclaimer, the term of this patent is extended or adjusted under 35 U.S.C. 154(b) by 1445 days.

(21) Appl. No.: 11/996,840

(22) PCT Filed: Jul. 25, 2006

(86) PCT No.: PCT/FR2006/001812
§ 371 (c)(1),
(2), (4) Date: Nov. 4, 2009

(87) PCT Pub. No.: WO2007/012750
PCT Pub. Date: Feb. 1, 2007

(65) Prior Publication Data
US 2011/0168632 A1    Jul. 14, 2011

(30) Foreign Application Priority Data

Jul. 26, 2005    (FR) ...................................... 05 07952

(51) Int. Cl.
*B01D 15/18* (2006.01)
*G01N 30/46* (2006.01)

(52) U.S. Cl.
CPC ............ *B01D 15/18* (2013.01); *B01D 15/1857* (2013.01); *B01D 15/1864* (2013.01); *B01D 15/1871* (2013.01); *G01N 30/461* (2013.01)

(58) Field of Classification Search
CPC ............... B01D 15/18; B01D 15/1857; B01D 15/1864; B01D 15/1871; G01N 30/461
USPC ............................... 210/635, 656, 659, 198.2
See application file for complete search history.

(56) References Cited

U.S. PATENT DOCUMENTS

| 4,274,967 | A |   | 6/1981  | Snyder et al. |
|-----------|---|---|---------|---------------|
| 4,970,002 | A | * | 11/1990 | Ando et al. .................... 210/659 |
| 5,434,298 | A | * | 7/1995  | Negawa et al. ............... 560/248 |
| 5,630,943 | A | * | 5/1997  | Grill .............................. 210/659 |
| 5,770,088 | A | * | 6/1998  | Ikeda et al. .................... 210/659 |
| 5,976,381 | A | * | 11/1999 | Lundell et al. ................ 210/656 |
| 6,063,284 | A | * | 5/2000  | Grill .............................. 210/659 |
| 6,093,317 | A | * | 7/2000  | Capelle et al. ............. 210/198.2 |
| 6,325,898 | B1 | * | 12/2001 | Blehaut et al. ................ 202/160 |
| 6,923,908 | B1 | * | 8/2005  | Thompson et al. ......... 210/198.2 |
| 2006/0243665 | A1 | * | 11/2006 | Couillard et al. ............. 210/635 |
| 2008/0135483 | A1 | * | 6/2008  | Strube et al. .................. 210/656 |

FOREIGN PATENT DOCUMENTS

CN            1327867 A   *  12/2001

* cited by examiner

*Primary Examiner* — Ernest G Therkorn
(74) *Attorney, Agent, or Firm* — Millen, White, Zelano & Branigan, P.C.

(57) ABSTRACT

The invention concerns a method for separating fractions of a mixture to be separated, in a device (1) comprising: several chromatography columns (21, 22, 23,) mounted in series; an open separation loop comprising in input a point for injecting (6) eluent in one of the columns and in output a point for drawing (8) a fraction of the mixture. The method includes the following steps: batch injection of the mixture to be separated in the open separation loop (4); collecting at least two fractions; offsetting at least one column of the eluent injecting and fraction drawing points (6, 8) of the separation loop (4). The invention also concerns a device for separating fractions of a mixture to be separated.

30 Claims, 12 Drawing Sheets

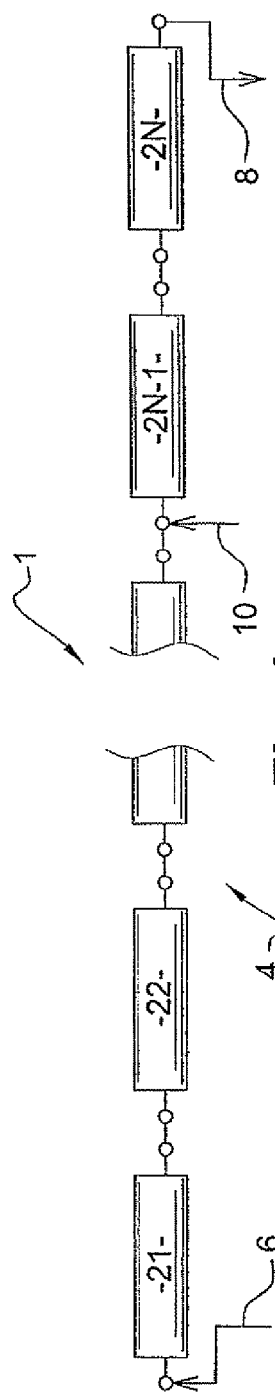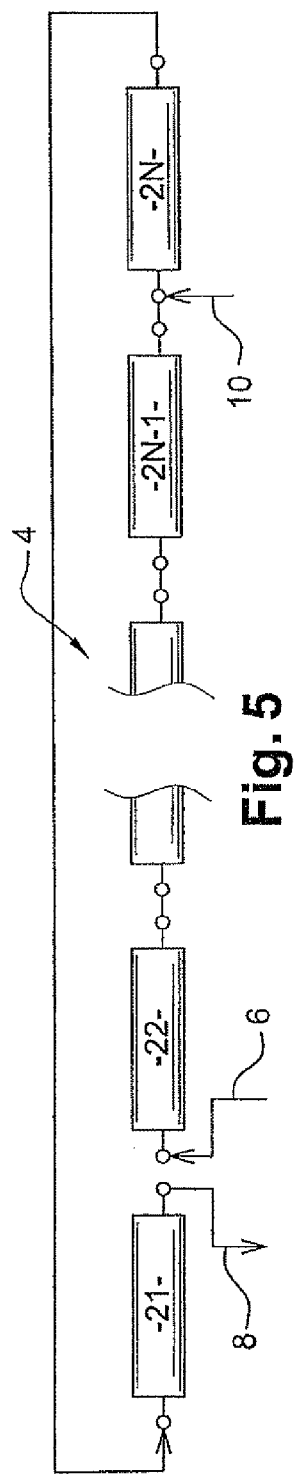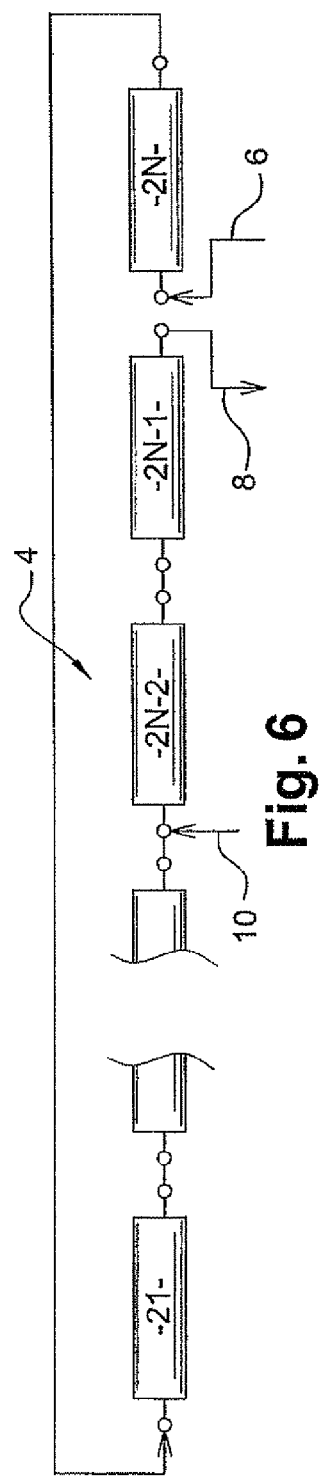

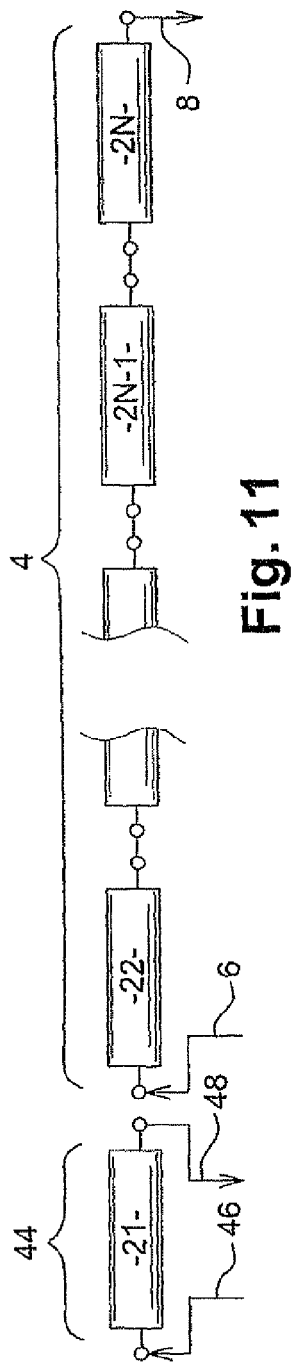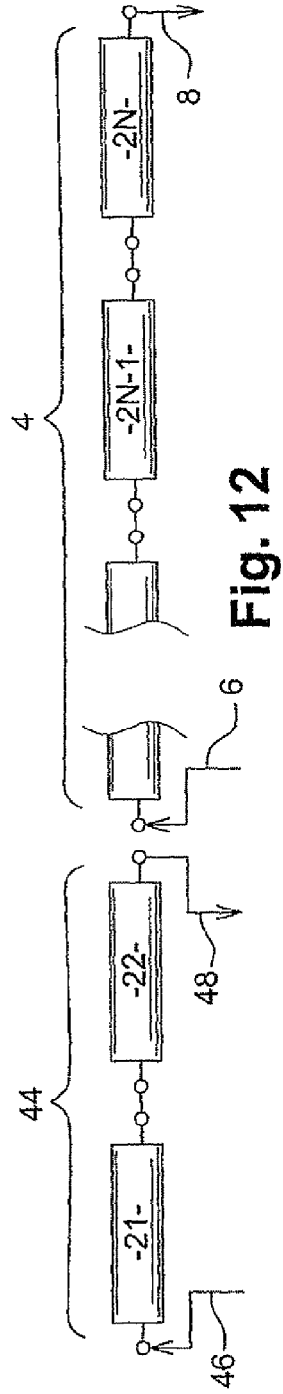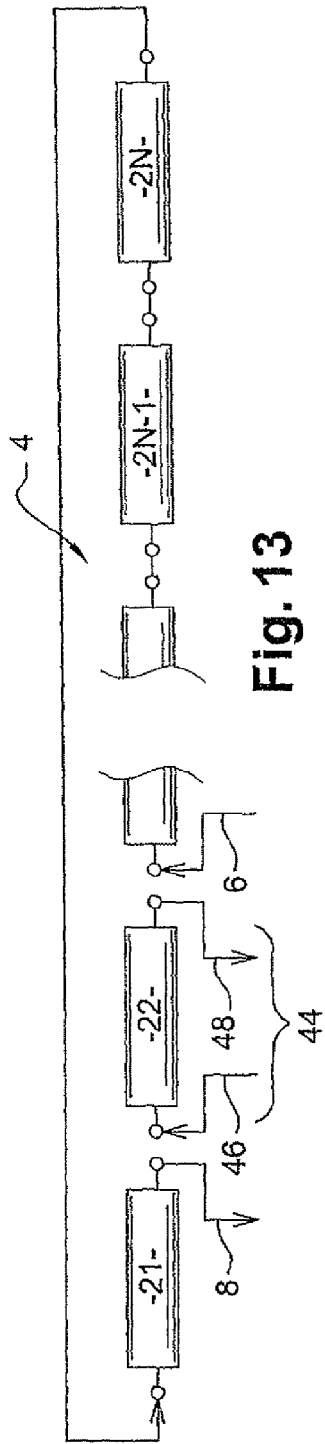

METHOD AND DEVICE FOR SEPARATING FRACTIONS OF A MIXTURE

REFERENCE TO RELATED APPLICATIONS

This application is a 371 of PCT/FR06/01812 filed Jul. 25, 2006

The present invention relates to a method and a device for separating fractions of a mixture by chromatography.

Chromatography is a separation method based on the difference in distribution of compounds of a mixture between a moving phase and a stationary phase. The compounds are separated by percolating a liquid, gaseous or supercritical solvent in a device (a column) filled with stationary phase.

This method is implemented as an analysis technique to identify and quantify the compounds of a mixture. It can also be implemented as a separation or purification technique.

According to the requirements, different chromatographic processes are used to carry out the purification of molecules. Some are described in the publication P. C. Wankat, Large scale Adsorption and Chromatography, CRC press, Boca-Raton, 1986, in the publication M. D. Le VAN DER LELY, G. Carta, C. Yon, Perry's Handbook Eng., Ed. 7, Mac-Graw-Hill, N-I, 1997, or in the publication of R. M. NICOUD and M. BAILLY, Choice and optimization of operating mode in industrial chromatography, Proceeding of the 9th International Symposium on preparative and industrial chromatography, PREP 92, April 1992, Nancy, p. 205-220.

One possible chromatographic process is the "batch" process. This process is based on the discontinuous injection of the mixture to be purified into a column filled with suitable stationary phase. The phase is percolated with an eluent, ensuring the migration and separation of the products in the column. The separated products are collected at the column outlet. The injections can be repeated while ensuring that the time between two injections allows the separation between successive injections to be maintained.

A variant of the "batch" process consists of recycling the non-purified fractions; the non-purified fractions are then reinjected at the column inlet. Injection and recycling phases are then alternated periodically.

The drawback of this "batch" process is that it performs poorly in terms of productivity. This productivity is generally low and the purified products are very diluted in the eluent.

Another possible chromatographic process is based on the principle of a 4-zone countercurrent in a "True Moving Bed" where, in a moving bed system because of a continuous countercurrent effect, the solid phases and eluents circulate continuously in countercurrent in a closed loop before fixed points for introducing the feedstock and eluent alternating with fixed points for drawing off a raffinate and extract.

For true moving bed operation, a countercurrent contact between the liquid and solid phases is set up in a device which can be divided into 4 different zones:
  Zone 1: everything situated between the eluent-injection and extract thaw-off lines;
  Zone 2: everything situated between the extract draw-off and feedstock-injection lines;
  Zone 3: everything situated between the feedstock-injection and raffinate draw-off lines;
  Zone 4: everything situated between the raffinate draw-off and eluent-injection lines.

Because of the inlet/outlet flows, the flow of liquid varies according to the zone, Q1, Q2, Q3, Q4 being the respective flows in zones 1, 2, 3 and 4, the flow of solid being constant.

In 1961, the company UOP patented a process allowing the simulation of the movement of the solid by an astute connection between the columns interconnected in a closed loop (U.S. Pat. No. 2,985,589 and U.S. Pat. Nos. 3,291,726, 3,268, 605). This process, called "Simulated Moving Bed" (SMB), then allows the practical realization of the true moving bed. It is characterized in that points for introducing the feedstock and eluent are periodically advanced downstream (in the circulation direction of the main fluid) whilst raffinate and extract draw-off points are advanced simultaneously and according to the same increment (at least one column for example). Operation is in synchronous mode. All the inlet and outlet lines are therefore moved simultaneously in each period $\Delta T$ and the cycle time, the time at the end of which they return to their initial position, is equal to $Nc \times \Delta T$, $Nc$ being the total number of columns. In SMB systems, the injection into the inlet lines and the drawing-off at the outlet lines are carried out continuously. The flow rate in the extract line is in principle strictly less than the flow rate in zone I such that the flow rate in zone II is not zero, similarly the raffinate flow rate is strictly less than the flow rate in zone III such that the flow rate in zone IV is not zero. The simulated moving bed is known for example from document U.S. Pat. No. 2,985,589.

SMB variants with 5 zones are described in the document Separation Science and Technology, Volume 2, chapter 13: Simulated Moving Bed chromatography for biomolecules, R. M Nicoud. They have in common a synchronous movement of the inlet/outlet lines as well as a continuous injection of the feedstock to be treated.

Another possible chromatographic process is the process for separation by chromatography in a simulated moving bed with correction of hold-up volume by desynchronization of the periods. This process is disclosed in FR-A-2 721 528.

In this process, the disturbances of the compositions of an extract (EA), or of a raffinate (RB), due to the hold-up volume introduced by at least one pump (P) for recycling a liquid, supercritical or gaseous mixture in a closed loop of column sections, or due to the degradation of their separation property each time that an injection or drawing-off current passes from a position in front to a position behind each of the hold-up volumes of the loop or each of the sections the separation properties of which are reduced, are corrected. Firstly, the duration of connection of said current to the loop is increased to an appropriate value, and then when the current passes from the position behind the hold-up volume or reduced section connection, to the following position, said period of connection is reduced such that said duration reassumes the value which would have been applied if each of the hold-up volumes had been disregarded or the degradations of separation properties had been disregarded. The injections are continuous in this process.

Another possible chromatographic process is the VARICOL process. This process is disclosed in particular in documents FR-A-2 785 196, U.S. Pat. No. 6,375,839, U.S. Pat. No. 6,136,198, U.S. Pat. No. 6,413,419 or U.S. Pat. No. 6,712,973. This document describes a process for separating at least one compound from a mixture containing it in a device having a set of chromatographic columns or chromatographic column sections containing an adsorbent, mounted in series and in a closed loop. The loop has at least one feedstock injection point, one raffinate draw-off point, one eluent-injection point and one extract draw-off point. In the device, a chromatographic zone is determined between an injection point and a draw-off point or vice-versa; at the end of a given period of time, the set of injection and draw-off points is shifted by one column or column section in a given direction defined relative to that of the flow of a main fluid circulating through the loop. During said period, the different injection and draw-off points are shifted by one column or column section at different times such that the length of the zones defined by said different points is variable.

In the VARICOL process, the different injection and drawing-off lines are shifted asynchronously. The injections of the eluent, the mixture to be treated and the drawing-off of extract and raffinate are continuous.

Another possible chromatographic process is the three-zone SMB. The process is implemented in a device having several chromatography columns interconnected in series. Two implementations are described in the documents Separation Science and Technology, Volume 2, chapter 13: Simulated Moving Bed chromatography for biomolecules, R. M Nicoud, Simulierte GegenStrom-Chromatographie, Chem. Ing. Tech. 66 (1994) No. 10, Deckert & Arlt, Comparative Study of Flow Schemes for a simulated Countercurrent Adsorption Separation Process, AIChE Journal, November 1992, Vol 38, No. 11, Ching, Chu, Hidajat & Uddin, Preparative resolution of praziquantel enantiomers by simulated countercurrent chromatography, Journal of Chromatography, 634 (1993) 215-219, Ching, Lin & Lee, Countercurrent and Simulated Countercurrent Adsorption Separation Processes, Chemical Engineering Science, Vol 44, No 5, pp 1101-1038, 1989, Ruthven & Ching.

In a first implementation, zone 4 of the SMB is eliminated: all of zone 3 is collected at the raffinate. The advantage of this device is the use of fewer columns by dispensing with the columns in zone 4. It has been shown however that this device causes a higher consumption of eluent and a greater dilution of the product collected at the raffinate than in a 4-zone SMB.

In a second implementation of this process, the fluid at the outlet of a column is directed towards the inlet of a following column, with the exception of a first point in the system for which the outlet of a column is collected fully at the extract, an eluent being injected directly into the inlet of the following column and with the exception of another point in the system for which the outlet of a column is collected fully at the raffinate, a purge liquid being injected directly into the inlet of the following column from where the raffinate is drawn off.

In the different implementations of the three-zone SMB, the injection of the mixture and the injection of eluent or eluents are carried out continuously. The inlet/outlet points are shifted by one column at fixed time intervals in a synchronous manner.

Another possible chromatographic process is the two-zone SMB. The document *Two Section Simulated Moving Bed Process*, Kwangnam Lee, Separation science and technology, 35(4), pp 519-534, 2000 describes this process. The process is implemented in a device having several chromatography columns interconnected in series. The fluid at the outlet of a column is directed towards the inlet of a following column, with the exception of a point in the system for which the fractions at the outlet of a column are collected. The injection of the mixture and the injection of the eluent are carried out continuously. The eluent injection point, the mixture-injection point and the point for collecting the fractions are shifted by one column at fixed time intervals, in a synchronous manner. Furthermore, there are only two zones having different flow rates of fluid, namely a zone before the mixture-injection point and a zone after the mixture-injection point.

A two-zone SMB process has also been described in the document *Two-zone SMB Process for Binary Separation*, Weihua Jin and Phillip C. Wankat, Ind. Eng. Chem. Res. 2005, 44, 1565-1575. This document describes another type of two-zone SMB. During a first stage, a mixture is introduced between zones I and II assembled in a closed loop, whilst part of the desorbent is recycled from zone I towards zone II and another part of the desorbent collected at the outlet of zone I is sent to a reservoir. During a second stage (without the introduction of the mixture) a fresh desorbent and the contents of the reservoir are used to produce the fractions. The raffinate is drawn off at the outlet of zone I and the extract is drawn off from zone II. At the end of the second stage, the points are switched and the process is repeated.

Another possible chromatographic process is the "Improved Simulated Moving Bed" process. This process is disclosed in particular in documents EP-A-0 342 629 or U.S. Pat. No. 5,064,539. The process alternates a stage of operating in a closed loop with an internal flow without any drawing-off or injection and a stage of operation with injection of feedstock flows and eluent and drawing-off of the flow of extract and raffinate.

Yet another possible chromatographic process is the Cyclojet process. This process can be applied to a column; it is disclosed in document EP-A-0 981 399. This document describes a cyclic chromatographic process using a single column comprising, during each cycle, a permanent periodic regime achieved by alternating successively:

a phase for collecting the least-retained raffinate or fraction;

a phase for recycling during which the feedstock is injected;

a phase for collecting the most-retained extract or fraction.

The injection of the feedstock is carried out by means of a loop which is:

loaded with feedstock by a loading device;

switched within the chromatographic device when it is in the recycling phase;

rinsed with eluent once the collection of the extract has begun, the loop is then again capable of being switched towards the loading device.

The drawback of this process is that the injection is carried out during the recycling stage, which makes it necessary to use an injection loop.

The Cyclojet process can also be applied to two columns; it is described in document EP-A-0 876 936. This document describes a preparative chromatographic cyclic process comprising in a permanent regime:

(a) the establishment of a chromatographic profile circulating in a figure of eight, between two chromatographic columns, wherein said chromatographic profile never passes through an elution pump;

(b) discontinuous and periodic injection of a mixture comprising at least two fractions into said circulation profile; and (c) collection, in discontinuous and periodic manner, of at least two enriched fractions from said circulation profile.

The principle is therefore based on the use of an external recycling system making it possible to avoid the transit of the recycled fraction in the elution pump.

The disadvantage of this process is the use of two columns without making it possible to separate two times more product than for a system with one column. The equivalent of one column is constantly unused for separation in this external recycling mode. Moreover, the two columns being eluted in series, the loss of feedstock during operation is doubled compared with the system with one column.

The aim of the invention is to purify at least one product of a mixture to be treated on a simple device having a reduced number of columns, namely at least two columns. The invention allows the use of several injection devices: pump or injection loop. The invention also maximizes the use of the columns for the separation.

For this purpose, the invention proposes a method for separating fractions of a mixture to be separated in a device having:
- several chromatography columns mounted in series,
- an open separation loop and comprising at the inlet a point for injecting eluent into one of the columns and at the outlet a point for drawing-off a fraction of the mixture, the method comprising the stages of:
- discontinuous injection of the mixture to be separated into the open separation loop,
- collection of at least two fractions,
- shifting by at least one column the points for injecting the eluent and for drawing off the fraction from the separation loop.

According to a variant, the mixture-injection stage is carried out independently of the collection and shifting stages.

According to a variant, the mixture is injected at the inlet of a column which is different from the column into which the eluent is injected.

According to a variant, the mixture is injected into the separation loop at a point distant from the eluent-injection and collection points of at least one column.

According to a variant, the shifting of the eluent-injection and collection points is carried out in the direction of flow of the mixture to be separated in the columns.

According to a variant, at least two fractions are collected successively at the collection point of the separation loop.

According to a variant, the device comprises two columns in series, the inlet of separation loop being at the inlet of one of the columns and the outlet of the separation loop being at the outlet of the other column, the collection stage comprising the collection of two fractions at the draw-off point at the outlet of the separation loop, one of the fractions, the extract, being more retained in the columns than the other fraction, the raffinate, which is less retained in the columns.

According to a variant, during the shifting stage, the eluent-injection and draw-off points of the separation loop are shifted at different times.

According to a variant, during the shifting stage, the eluent-injection point of the separation loop is shifted by at least one column towards the draw-off point of the separation loop, in the direction of flow of the mixture to be separated in the columns, at least one column remaining between the injection point and the draw-off point.

According to a variant, during the shifting stage, the draw-off point of the separation loop is shifted in the direction of the direction of flow of the mixture to be separated in the columns, by as many columns as the eluent-injection point of the separation loop has been shifted.

According to a variant, the device also comprises at least one other loop, every other loop being open and comprising at the inlet another eluent-injection point and at the outlet another collection point, the method comprising, after the shifting of the eluent-injection point of the separation loop by at least one column, the shifting by at least one column of the draw-off point of one of the other loops.

According to a variant, after the shifting of the eluent-injection point of the separation loop by at least one column, at least one other loop appears with at least one shifted column, every other loop having appeared being open and comprising at the inlet another injection point and at the outlet another draw-off point.

According to a variant, each loop is eluted with eluents of a different kind or of different compositions.

According to a variant, during the shifting stage, the eluent-injection and draw-off points of the separation loop are shifted simultaneously.

According to a variant, the device also comprises at least one other loop, every other loop being open and comprising at the inlet another eluent-injection point and at the outlet another draw-off point, the collection stage also comprising collection at the draw-off point of every other loop.

According to a variant, each loop is eluted with eluents of a different kind or of different compositions.

According to a variant, during the shifting stage of the eluent-injection and collection points of the separation loop, the other eluent-injection and collection points of every other loop are shifted simultaneously with the eluent-injection and collection points of the separation loop.

According to a variant, each loop other than the separation loop ensures the desorption of the mixture fractions most retained in the columns or the regeneration of the columns.

According to a variant, the eluent-injection and draw-off points of the separation loop are contiguous.

According to a variant, the eluent-injection and draw-off points of the separation loop are not contiguous.

According to a variant, the eluent-injection and draw-off points are separated by at least one other separation loop.

According to a variant, the injection is only carried out during certain periods.

According to a variant, the method is cyclical.

The invention also relates to a device comprising
- several chromatography columns mounted in series,
- an open separation loop comprising at the inlet an eluent-injection point in one of the columns and at the outlet a point for drawing-off a fraction of a mixture to be separated, as well as a mixture-injection point,
- a control suited to the discontinuous injection of a mixture to be separated into the open loop and the shifting by at least one column of the positions of the injection and drawing-off points.

According to a variant, the control is suited to the shifting of the positions of the eluent-injection and draw-off points of the separation loop in a simultaneous manner.

According to a variant, the control is suited to the shifting of the positions of the eluent-injection and draw-off points of the separation loop at different times.

According to a variant, the mixture-injection point is at the inlet of a column different from the column where the eluent-injection point is located.

According to a variant, the device also comprises, between the draw-off point and the eluent-injection point of the separation loop, at least one other loop, every other loop being open and comprising at the inlet an eluent-injection point and at the outlet a draw-off point.

According to a variant, the control is suited to shift the eluent-injection and collection points of every other loop, simultaneously with the eluent-injection and collection points of the separation loop.

According to a variant, every other loop is of the desorption loop or regeneration loop type.

According to a variant, the device also comprises a stationary phase in the columns.

According to a variant, the device comprises an injection loop or an injection pump for the injection of the feedstock.

According to a variant, the device comprises a pump for the injection of the feedstock and as many pumps as there are eluents.

According to a variant, a pump is inserted between at least two of the columns of the device.

According to a variant, the device is for the implementation of the method as described previously.

Other features and advantages of the invention will become apparent on reading the following description of the embodiments of the invention, given solely by way of example and with reference to the drawings which show:

BRIEF DESCRIPTION OF THE DRAWINGS

FIGS. 4 to 7, the operation of FIGS. 1 to 3 applied to more than two columns;

FIGS. 8 to 16, the operation of the preceding figures, with more than one loop;

DESCRIPTION OF THE PREFERRED EMBODIMENTS

Figure 1:
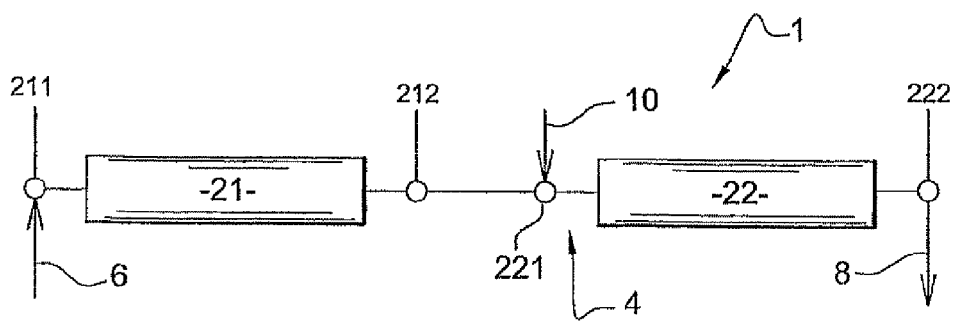
FIGS. 1 to 3, the operation of the method and of the device according to the invention.

The invention relates to a method for separating fractions of a mixture to be separated. The method is applied to a device having several chromatography columns mounted in series. The device comprises a separation loop within the columns. The separation loop is open and comprises at the inlet an eluent-injection point and at the outlet a point for drawing-off a fraction of the mixture to be separated. The method comprises stages of discontinuous injection of a mixture to be separated into the open separation loop, collection of at least two fractions and shifting by at least one column the injection and draw-off points of the separation loop. The method is simple.

The method makes it possible to exploit the whole of the stationary phase unlike the two-column Cyclojet method which requires constantly having one of the two columns full of eluent.

The collection of fractions from the device takes place at different points of the device according to the embodiments. In a two-column device the collection of the fractions can be carried out at the draw-off point of the separation loop; in a device with more that two columns, it is possible to envisage collecting a fraction at the draw-off point of the separation loop, since one or more other fractions are collected at other points of the device.

In what follows, it is possible to envisage that the mixture is actually injected inside a column divided into column sections, and not only at the column inlet. The same applies for the eluent injection and fraction collection. In what follows, the term column is used to designate a chromatographic column or a chromatographic column section.

The columns are capable of accommodating a stationary phase (liquid or solid) or chromatographic bed. The stationary phase makes it possible to adsorb at least one fraction of the mixture to be separated; fractions are referred to as being more or less retained by the stationary phase. In the case of a binary mixture, the fraction most retained by the stationary phase is the extract, the fraction least retained by the stationary phase is the raffinate. By way of example the eluents which can be used are fluids: liquid, gaseous, supercritical or subcritical. The eluent used can be a single-phase fluid constituted by at least one gaseous product at ambient pressure and temperature. The eluent used can be a fluid containing at least carbon dioxide in the supercritical state. The eluent used can be a homogeneous fluid containing at least carbon dioxide. The eluent can be recycled by means chosen from the group consisting of distillation, evaporation and the use of membranes. By way of example, the stationary phases can be a liquid or a solid, an adsorbent in the general sense, such as a molecular sieve, zeolithic for example, used in the adsorption processes, or an adsorbent such as a polymer resin. The stationary phases can also be an ion-exchange resin used to carry out ion exchange or sugar purification. It is also possible to use a stationary phase on a silica base, a reverse phase adsorbent or a chiral phase. The range of pressures in which separations are carried out can be situated between 0.1 and 50 MPa and preferably between 0.1 and 30 MPa. The temperature is generally comprised between 0 and 100° C.

Figure 2:
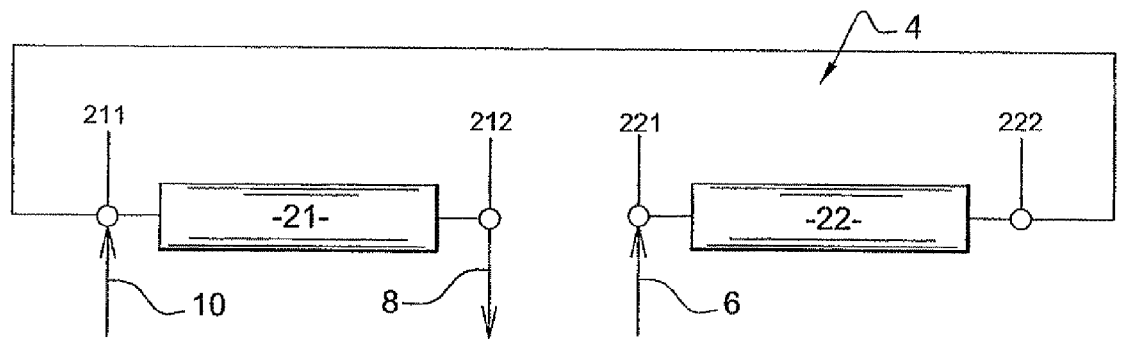
Figure 3:
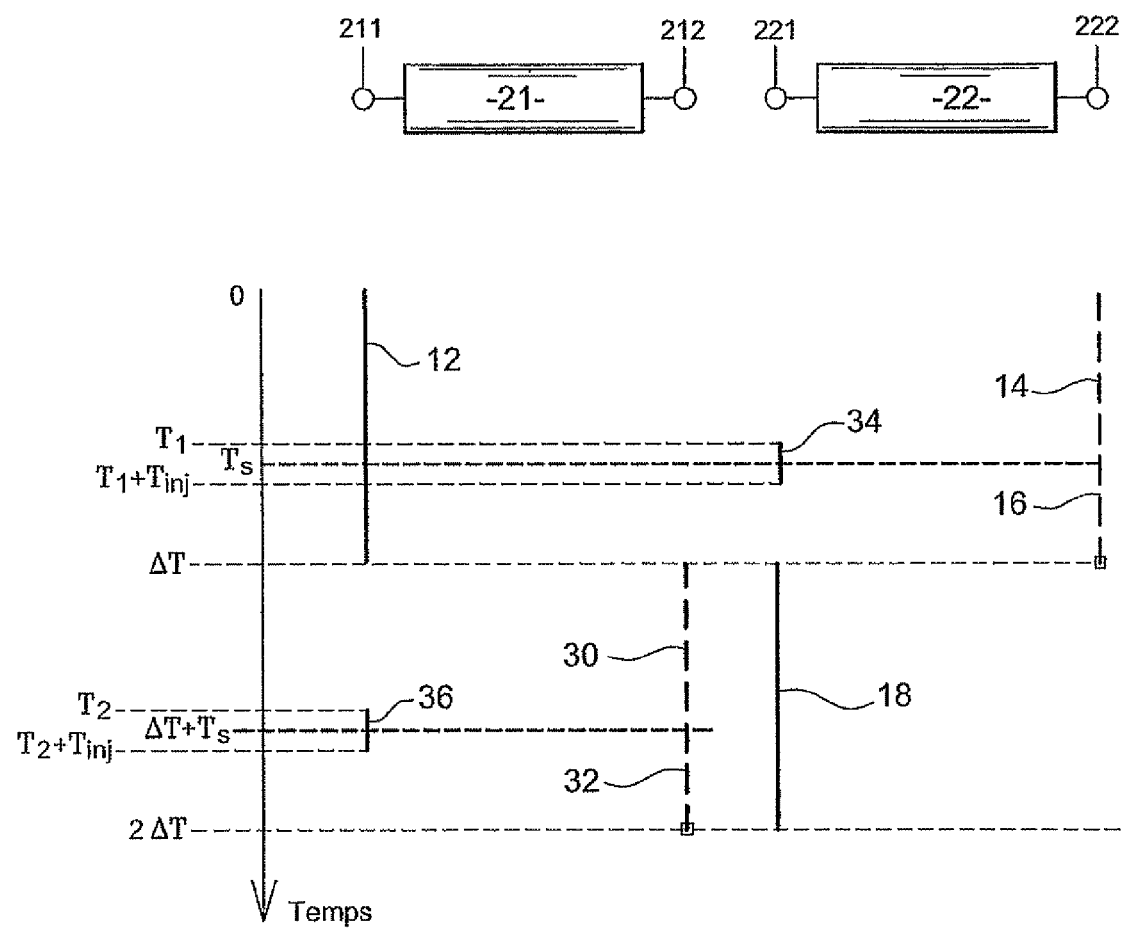

FIGS. 1 to 3 show a chromatography device 10. This device makes it possible to separate fractions F1, F2, F3 etc. of a mixture (or feedstock) to be separated. The mixture can be binary, i.e. comprising two compounds; however, the mixture can also contain more than two compounds. According to FIG. 1, the device 1 comprises two chromatography columns 21 and 22; the device can contain N columns with N>2. The columns are mounted in series, in the sense that the column 21 has an outlet 212 contiguous with the inlet 221 of the other column 22; the outlet 212 of column 21 can be connected to the inlet 221 of column 22, in such a manner as to circulate a fluid between the two columns 21 and 22. Hereafter, by columns in series is meant columns wherein the outlet of one column is capable of being connected to the inlet of another column, in order to circulate a fluid between the columns.

The columns 21 and 22 form a separation loop 4, this loop allowing the dissociation of a fraction composing the mixture to be separated. The loop 4 is open; the loop 4 has an inlet point and an outlet point. The loop is open because the inlet and the outlet of the loop are not connected. There is therefore no fluid circulating between the inlet and the outlet of the loop. The advantage of an open loop is that this facilitates the operation of the device and of the method: apart from the injection stage, the flow rate in the separation loop is the same. This makes the operation of the device simple; unlike in an SMB for example there is no need for example to manage collection between different zones since in this case there is only one zone.

Moreover, by open-loop operation, the device and the method make it possible to constantly collect one or more purified fractions, unlike the recycling processes of the Cyclojet, ISMS, or 2-zone SMB type with discontinuous injection involving a stage of closed-loop circulation.

According to FIG. 1, the inlet of the loop 4 is the inlet 211 of column 21 and the outlet of the loop 4 is the outlet 222 of column 22. It can be seen that the inlet 211 is not connected to the outlet 222. Moreover, the inlet and the outlet of the loop can be contiguous; the inlet and the outlet of the loop can then be linked during a shifting stage as described hereafter by opening the loop at another place. The inlet and the outlet of the loop may not be contiguous; indeed the inlet and the outlet can be separated by at least one additional loop, as described hereafter. The advantage of an open loop is that implementation is simple; an open loop also leaves a choice regarding the ways of injecting a fluid into the loop, by using for example a pump or an injection loop.

The loop comprises at the inlet an injection point 6 and at the outlet a draw-off point 8. At the injection point 6 of the loop 4, an eluent is injected into the loop. The eluent makes it possible to carry out the separation of fractions by elution within the columns; in particular, the eluent makes it possible to entrain the different compounds of the mixture which are more or less retained by the stationary phase. At the draw-off point 8 of the loop 4, a stage of drawing-off of at least one fraction composing the mixture to be separated is carried out. It is thus possible to accommodate a fraction which is more retained by the stationary phase or a fraction which is less retained by the stationary phase. However, in this two-column device, it is preferable to collect at least two fractions (F1, F2, . . . , Fj) at the draw-off point 8. In particular, the fractions are collected successively at the same draw-off point 8; the advantage is therefore that the collection or injection operation does not have to use a flow-rate regulation device—indeed the collection flow rate is equal to the liquid flow rate in the column.

FIG. 1 also shows an injection point 10 for a mixture to be separated in the separation loop 4. The injection of the mixture is discontinuous, in the sense that the injection of mixture is interrupted in time. This makes it possible to use a small number of columns; indeed, during injection, the column fills with the mixture to be separated and if the injection is too long there is a risk of reducing the purity of at least one of the collected fractions.

The injection of the mixture is carried out into the loop 4 which is open. The process of injection of mixture (or feedstock) is variable. It can be carried out by feedstock injection, stopping the injection of eluent; the feedstock injection flow rate can be different from the flow rate of the eluent pump. The injection of the mixture can also be done by a feedstock pump without stopping the eluent flow. The flow rate of the feedstock pump can be different from the flow rate of the eluent pump. The mixture can also be injected by means of an injection loop containing the mixture. An injection loop makes it possible to add a volume containing the mixture to the separation loop.

The advantage of this process where the injection is carried out within an open loop is therefore that different injection devices can be used: an injection pump or loop, unlike a 1-column Cyclojet type device or 2-zone SMB. For a one-column Cyclojet for example, a pump cannot be used with a liquid eluent as the injection takes place in a closed circuit; the choice of the injection loop is then obligatory. In the case of the 2-zone SMB with discontinuous injection, the injection is carried out by a pump but the device requires the use of an additional reservoir, as the injection also takes place in a closed loop.

Moreover, the mixture injection stage can be carried out independently of the collection and shifting stages; the mixture can be injected at any place and time relative to the position of the other injection and draw-off points. The mixture can be injected at any column inlet. The injection of mixture can also be carried out only during certain periods. The user then has greater freedom to adjust the injection of mixture.

Preferably, the mixture is injected at the inlet of a column which is different from the column where the eluent is injected. In the direction of flow, the eluent is therefore injected further upstream than the mixture. The advantage is that a better separation of the fractions is obtained. Moreover, it is also preferable for the mixture to be injected into the separation loop 4 at a point distant from the injection 6 and draw-off points 8 of a column; in other words the mixture-injection point 10 is produced in the middle of the separation loop 4. In FIG. 1, the mixture-injection point 10 is between the two columns 21 and 22, at the inlet 221 of column 22. In a device comprising a greater number of columns, the feedstock injection is carried out at a distance of at least one column from the point where the eluent and fraction collection are located.

FIG. 2 shows that a shifting of the injection 6 and draw-off 8 points is carried out in the device and during the process. Indeed, the injection point 6 is shifted by one column, and is then at the inlet 221 of column 22; also, the draw-off point 8 is shifted by one column, and is then at the outlet 212 of column 21. Moreover, the outlet 222 of column 22 is connected to the inlet 211 of column 21, in order to allow the fluid to circulate from column 22 to column 21. Moreover, the loop 4 is kept open as the outlet 212 of column 21 is no longer connected to the inlet 221 of column 22. There has therefore also been a shifting of the inlet and of the outlet of the loop 4. In FIG. 2, the mixture-injection point 10 is between the two columns 22 and 21 at the inlet 211 of column 21.

The shifting of the injection and draw-off points is adjusted to the speeds of movement of the species within the device, thus making it possible to collect at least one fraction when its purity or its enrichment is sufficient.

The shifting is preferably in the direction of flow of the mixture to be separated in the columns. The shifting of the injection and draw-off points in the direction of flow makes it possible to follow the movements of the products in the process, allowing them to be distributed in the loop 4 and thus to better exploit the stationary phase of the system. For these reasons, the yield of the device and of the method is improved.

The shifting of the injection 6 and draw-off 8 points can be by one column; this is the case in FIG. 2. However, it is also possible to envisage shifting the injection 6 and draw-off 8 points by more than one column, when the loop comprises more than two columns. The advantage is for example to be able to simulate a column of volume V by smaller columns the sum of the volumes of which is equal to V.

FIG. 3 is an example of a diagram summarizing the injection and drawing-off process as well as the shifting of the injection and draw-off points as described previously in a device comprising an open loop with two columns. By the description of this figure, it is shown that the operation of the device is cyclical, and that a cycle comprises as many periods as there are columns in the separation loop. It is also noted that the fractions are collected at the same point. In a general manner hereafter, a period $\Delta T$ is then defined as the smallest time interval at the end of which each of the injection and draw-off points have been shifted by the same number of columns.

FIG. 3 shows the two columns 21 and 22 along which the mixture is separated. Time is also represented along a vertical axis. This time corresponds to the mixture or eluent injection time into the loop 4 as well as to the collection time of at least one fraction of the mixture.

It is accepted that at time T=0, the device operates under a steady regime; for this purpose there have already been injections of mixture and eluent as well as collection of one or more fractions.

At T=0, the inlet of the loop 4 corresponds to the inlet of column 21 and the outlet of the loop 4 corresponds to the outlet of column 22. FIG. 3 shows an injection 12 of eluent at the inlet of the loop, at the column inlet 21 and collections 14 and 16 of fractions at the loop outlet, at the column outlet 22. The eluent injection 12 and the collections 14 and 16 of fractions can take place throughout a first period $\Delta T$. The collection 14 of a fraction is followed at time Ts by the collection 16 of another fraction. In the case of a binary mixture, it is possible to first collect the extract which is the most retained fraction then to collect the raffinate which is the least retained fraction. Thus, in the case of a binary mixture, the period $\Delta T$ can be made up of two sub-periods of collection of each of the fractions. It is also possible to envisage collecting more than two fractions if appropriate, the period $\Delta T$ then being made up of as many sub-periods as fractions.

It can also be envisaged that during a period, the injection and/or collection stages are interrupted.

At the end of the first $\Delta T$, the injection 6 and draw-off 8 points are shifted by one column as described in connection with FIG. 2. The inlet of the loop 4 now corresponds to the inlet of column 22 and the outlet of the loop 4 corresponds to the outlet of column 21. Then a second period $2\Delta T$ begins; an injection 18 of eluent takes place at the inlet of the loop, at the inlet of column 22 as well as collections 30 and 32 of fractions at the loop outlet, at the outlet of column 21. The eluent injection 18 and the collections 30 and 32 of fractions can take place throughout the second period 2ΔT. Thus, the collection 30 of a fraction can be followed at time ΔT+Ts by the collection 32 of another fraction. The collection time of the different fractions can be identical from one period to another or different.

It is noted in FIG. 3 that a new shifting at the end of the second period 2ΔT leads the device to be once again in the configuration of FIG. 1; the separation process described operates cyclically, the device being in an initial configuration at the end of each cycle. Each cycle can itself be divided into as many periods as the loop has columns; in FIG. 3, the cycle comprises two periods as the device described has two columns. Also, each period can be divided into as many sub-periods as there are fractions to be collected for each outlet line. There is therefore one or more collection of fractions over a period. Moreover, the chromatography profile of the fractions of the mixture extends over all the columns of the separation loop 4 which makes it possible to exploit all the columns of this loop during the separation.

FIG. 3 also shows the injection of the mixture into the device. The injection can be periodic (at each period). During the first period ΔT, the injection of mixture 34 takes place at time T1. The injection of mixture 34 is stopped for example at time T1+Tinj. The injection of mixture 34 is therefore discontinuous as it does not last throughout the period. During the injection, according to the injection process, it is possible either to stop or to maintain the flow rate of the eluent at the inlet 211 of column 21. During the second period 2ΔT, the injection of mixture 36 takes place at time T2. The injection of mixture 36 is stopped for example at time T2+Tinj. Once again, the injection of mixture 36 is discontinuous as it does not last throughout the second period. During the injection, according to the injection process, it is possible either to stop or to maintain the flow rate of the eluent at the inlet 221 of column 22. Preferably, the injection of mixture is periodic; this makes it possible to reinject fresh mixture in order for the device to operate permanently. Also the mixture injection stage 34 and 36 is carried out at any moment and at any point in relation to the collection stages 14, 16, 30, 32 and eluent-injection stages 12, 18. Thus the injection of mixture can commence at any moment during the period. It is also possible to envisage that the injection of mixture commences at the end of one period and is terminated at the start of the following period. Thus, the injection of mixture is independent of the positions and movements of the eluent-injection and draw-off points of the fractions. This is advantageous as it allows injection at any moment and at any point of the device.

The injection of the mixture can also be cyclical, a constant volume of mixture being injected at each complete cycle, a number of times less than the number of columns. Thus, a volume V can be injected once rather than a volume V/2 at each of the two periods in a 2-column device. Alternatively it is possible to inject two times a volume V rather than injecting a volume V/2 at each of the four periods into a four-column device. The advantage is then that of injecting a larger volume (simpler with a pump) or limiting the number of injection devices if loops are involved.

FIGS. 4 to 7 show the separation method applied to a device comprising N columns, with N>2. In FIG. 4, the loop 4 comprises N columns in series, the columns having an outlet which can be connected to the inlet of a following column. The outlet of one column can be connected to the inlet of a following column, with the exception of the outlet of column 2N which is not connected to the inlet of column 21 such that the loop 4 is open. At the inlet of the loop 4, the eluent-injection point 6 is at the column inlet 21. At the outlet of the loop 4, the point for drawing-off a fraction 8 is at the outlet of column 2N. Thus a fluid can circulate between the columns. The mixture-injection point 10 is represented by way of example between the columns 2N-1 and 2N-2. In FIG. 5, the injection 6 and draw-off 8 points are shifted by one column. The outlet of the column 2N is then connected to the inlet of column 21. The loop is open between columns 21 and 22. Finally, in FIG. 6, the injection 6 and draw-off 8 points have been shifted N-1 times; a new shifting by one column of the points 6 and 8 completes one operating cycle of the method. During this cycle, the mixture was injected in a discontinuous manner, an injection having taken place in FIG. 4 and then being interrupted.

Figure 7:
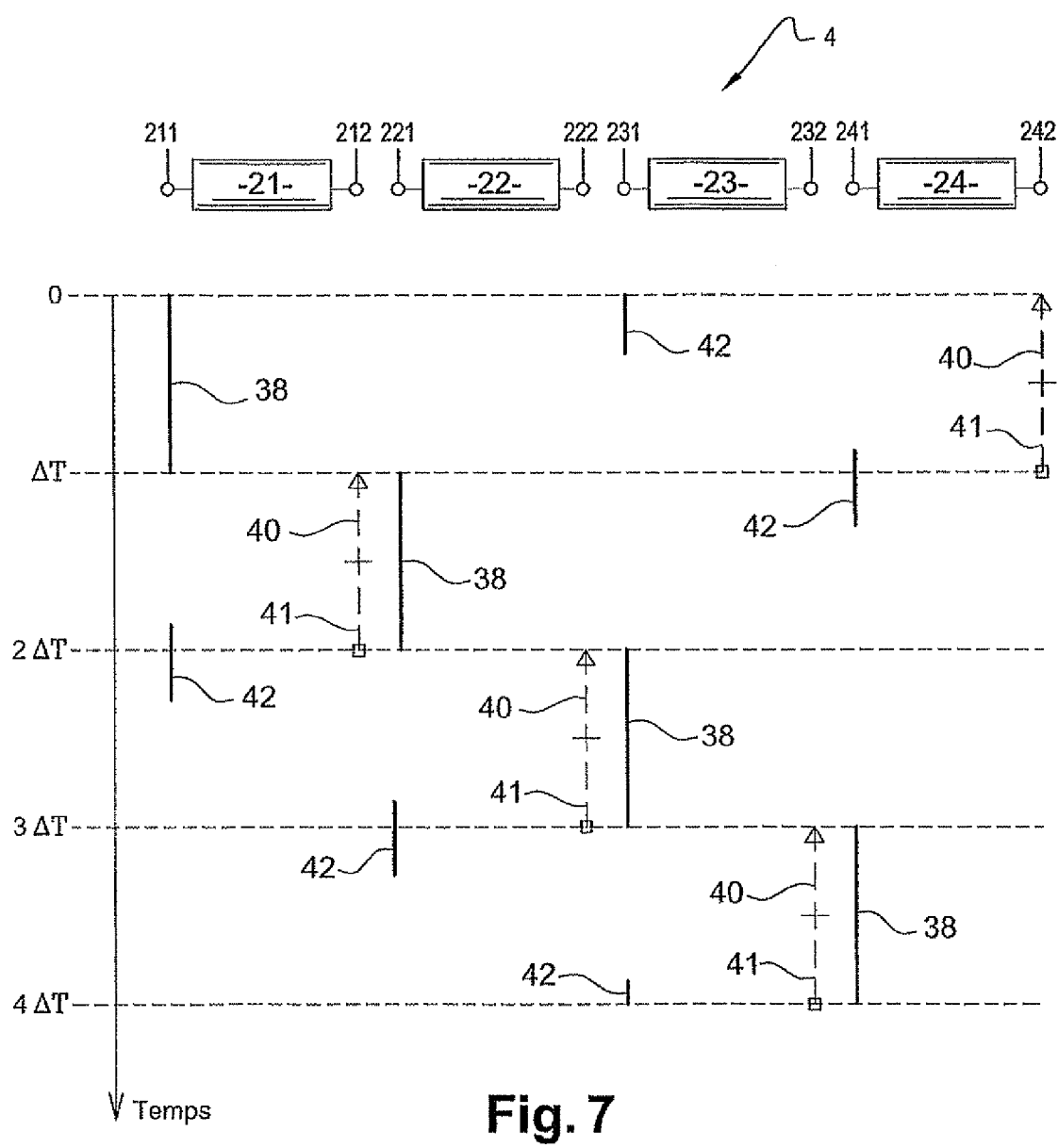

FIG. 7 is a diagram summarizing the injection and collection process as well as the shifting of the injection and draw-off points as described previously in a device comprising an open loop with four columns 21, 22, 23, 24. The operation of the method is over four columns. During each period, an eluent injection 38 and collections 40 and 41 take place throughout each period. Between each period, the points 6 and 8 are shifted, for example by one column. Thus, after four shifts, the points 6 and 8 are again in the initial position. In FIG. 7, it is shown that two fractions are collected successively during each period, by way of example.

Moreover, FIG. 7 shows discontinuous injections of mixture 42. The injections take place into the loop 4, between the columns 22 and 23. The injections are periodic as they take place each period. The injections of mixture 42 are carried out at any moment and at any point relative to the moments and places of injections 38 and collections 40 and 41. The injections of mixture are independent of the eluent injection and of the fraction collection. For example, the injections of mixture 42 are carried out straddling two periods, beginning at the end of one period and terminated at the start of the following period and the start of the injection of the mixture 42 does not take place in the middle of the loop whereas the end of the injection of the mixture 42, by the shifting of the points 6 and 8, takes place in the middle of the loop. According to the injection method, it is possible either to stop, or to maintain the flow rate of the eluent during the injection.

FIG. 7 shows that for a loop with 4 columns, a cycle comprises four periods ΔT, 2ΔT, 3ΔT, 4ΔT. At the end of these four periods, the points 6 and 8 are in the same positions as at the start of the cycle. Each period is then divided according to the number of fractions collected. In the figures, the two fractions are collected at the same draw-off point 8. Of course, more than two fractions can be collected at the same draw-off point.

According to FIGS. 3 and 7, the eluent-injection 6 and draw-off 8 points can be shifted simultaneously. These points 6 and 8 are shifted at the same time. Operation is synchronous. This makes it possible to simplify management of the shifting of the points. In the examples in FIGS. 1, 2, 4, 5, 6, the loop 4 is open and the inlet and the outlet of the loop 4 are contiguous; with simultaneous shifting of the points 6 and 8, the inlet and the outlet of the loop remain contiguous during the operating cycle.

Alternatively, the eluent-injection 6 and drawing-off 8 points can be shifted at different times. Operation is asynchronous. For example, the eluent-injection point 6 is shifted before the draw-off point 8. This makes it possible for example to release as many columns as the number of columns by which the injection point 6 has been shifted. These columns having left the loop can then be intended for an operation other than the separation of the mixture. As described hereafter, it is possible to create a desorption zone or a regeneration zone. A period ΔT is then defined as the smallest time interval at the end of which each of the injection and draw-off points have been shifted by the same number of columns.

Figure 8:
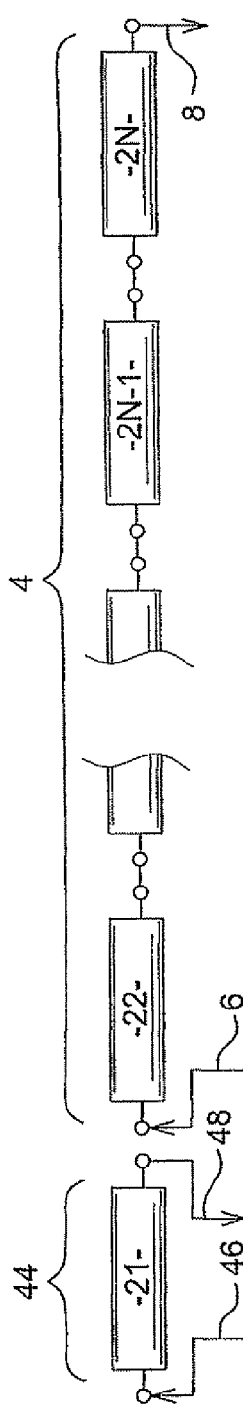
Figure 9:
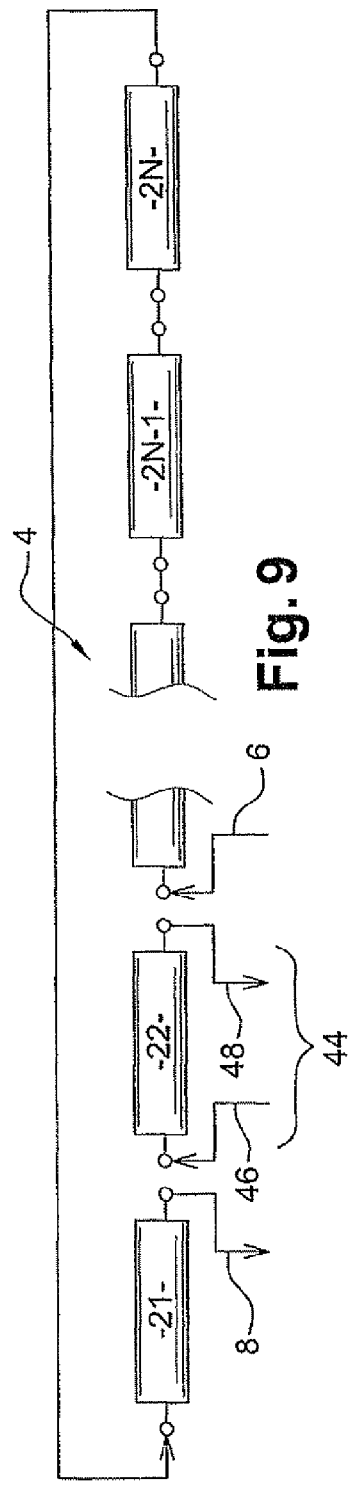
Figure 10:
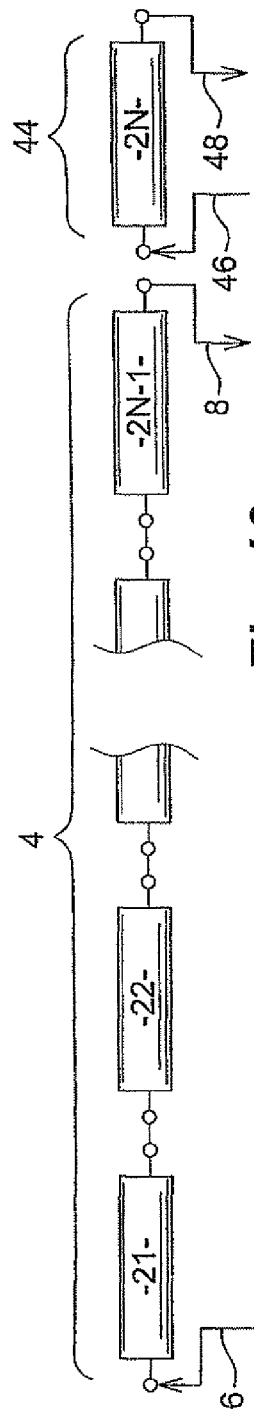

FIGS. 8 to 10 show a variant of the method and the device. In these figures, the device also comprises at least one other loop, or additional loop.

In these figures, the device 1 comprises N columns (N≥2) and two zones, namely a separation zone and an additional zone, for example, a desorption zone. The separation zone corresponds to the separation loop 4. The desorption zone corresponds to another loop 44, called a desorption loop. The separation loop 4 is open and comprises the columns 22 to 2N. At the inlet of separation loop 4, the injection point 6 is situated at the inlet of column 22; at the outlet of the separation loop 4, the draw-off point 8 is situated at the outlet of column 2N. The desorption loop 44 is also open and comprises the column 21. At the inlet of desorption loop 44, another injection point 46 is situated at the inlet of column 21; at the outlet of desorption loop 44, another draw-off point 48 is situated at the outlet of column 21. In the present case there are two loops 4 and 44 all of the columns of which are respectively in series.

At the inlet of separation loop 4 eluent is injected at the injection point 6; at the outlet of separation loop 4, at least one fraction of mixture can be collected at the draw-off point 8. At the inlet of desorption loop 44 eluent can be injected at the injection point 46; at the outlet of desorption loop 44, at least one fraction can be collected at the draw-off point 48. At least two fractions are collected from the device, at least one fraction being able to be collected at the outlet of each zone.

In FIGS. 9 and 10, the same process as in the preceding figures is applied to the device 1, to the extent that the two loops are shifted along the columns. The injection and draw-off points of each loop are shifted synchronously. In FIG. 9, the injection points 6 and 46 and the draw-off points 8 and 48 have been shifted by one column. Thus, the inlet and the outlet of each loop are shifted. It would be possible to shift the inlets and outlets by more than one column. In FIG. 10, the injection and draw-off points have been shifted N-1 times; the subsequent shifting of the injection and draw-off points allows the device to return to its initial position at the start of the cycle.

Applied to FIGS. 8 to 10, the method comprises a stage of collecting at least one fraction at the draw-off points 8 and 48 of the separation and desorption loops; the method also comprises a stage of shifting the injection points 6 and 46 and the draw-off points 8 and 48 of the separation and desorption loops.

The mixture to be separated can be injected discontinuously into the separation loop 4, independently of the injection and collection stages; preferably the mixture-injection point 10 is at the inlet of a column different from the column where the eluent is injected into the separation loop 4.

Preferably, the additional or desorption loop 44 allows the desorption of the most-retained fractions of the mixture in the stationary phase after shifting of the injection and draw-off points of the loops in the direction of flow of the fluid in the columns. It is possible for example to collect only one fraction at the outlet of desorption loop 44, such as the extract from a binary mixture which has been more retained by the stationary phase. The desorption loop 44 then allows the desorption of the extract.

It is also possible to envisage that the device includes, apart from the separation loop 4, several desorption loops, thus defining several desorption zones; each desorption loop is open with an injection point at the inlet and a draw-off point at the outlet. All of the columns are in series. The eluents at the inlet of each separation and desorption loop can have different compositions and flow rates. The eluent composition and flow rate can also vary during a period.

The additional loop or loops can comprise one or more columns.

The shifting of the injection and draw-off points of the separation loop 4 and of the additional, for example desorption, loop 44, can be synchronous, i.e. shifted at the same time or asynchronously, i.e. shifted at different times; the desorption 44 and separation 4 loops can then comprise a variable number of columns. In FIGS. 11 to 13, the operation is asynchronous, the number of columns of each loop being variable. This is advantageous for devices comprising a small number of columns, it is thus possible to define a desorption zone which contains on average over a period a non-integer number of columns the advantage then being that of finely distributing the columns in each of the zones of the process. The mixture-injection point 10 will not be described, but for this, reference may be made to the preceding figures.

The device comprises two loops, the separation loop 4 and the additional or desorption loop 44. FIG. 11 corresponds to FIG. 8. In FIG. 11, the desorption loop 44 comprises a column and the separation loop 4 comprises N-1 columns. Several fractions are collected from the device, at least one fraction being able to be collected at the outlet of each zone.

In FIG. 12, at the start of a first period, the injection point 6 of the separation loop 4 and the draw-off point 48 of the desorption loop 44 are shifted before the corresponding draw-off 8 and injection 46 points. The injection point 6 of the separation loop 4 and the draw-off point 48 of the desorption loop 44 are shifted by at least one column towards the corresponding draw-off 8 and injection 46 points, in the direction of flow of the mixture to be separated in the columns, at least one column remaining between the points 6 and 8 and between the points 46 and 48. The shifting is by one column, for example. The desorption loop 44 then comprises two columns and the separation loop 4 comprises N-2 columns.

In FIG. 13, at the end of the period, the draw-off point 8 of the separation loop 4 and the injection point 46 of the desorption loop 44 are shifted by as many columns as the number by which the points 6 and 48 have been shifted. The desorption loop 44 then comprises a column and the separation loop 4 comprises N-1 columns, as at the start of the period. Thus, the number of columns of each loop varies during the period. In the example of FIGS. 11 to 13, the number of columns in the desorption loop 44 varies during the period. It is therefore possible to manage a device having a non-constant number of columns in the desorption loop and in the separation loop over an operating period.

The period described in connection with FIGS. 11 to 13 can be repeated in order to complete an operating cycle at the end of which the device returns to the configuration of the initial positions of the injection and draw-off points of the loops. Similarly it is possible to provide more than one desorption loop and/or one or more regeneration-type loops.

Naturally the number of columns of the additional or desorption loop 44 can be different from the example given in FIGS. 11 to 13. The shifting at the end of the period of the points 8 and 46 can occur after a shifting by more than one column of the points 6 and 48. Similarly, the desorption loop 44 can have a number of columns developing in the manner of an accordion before returning at the end of the period to the same number of columns as at the start of the period.

In FIGS. 11 to 13 it is also possible to inject eluent containing concentrated extract at the injection point 6.

Figure 14:
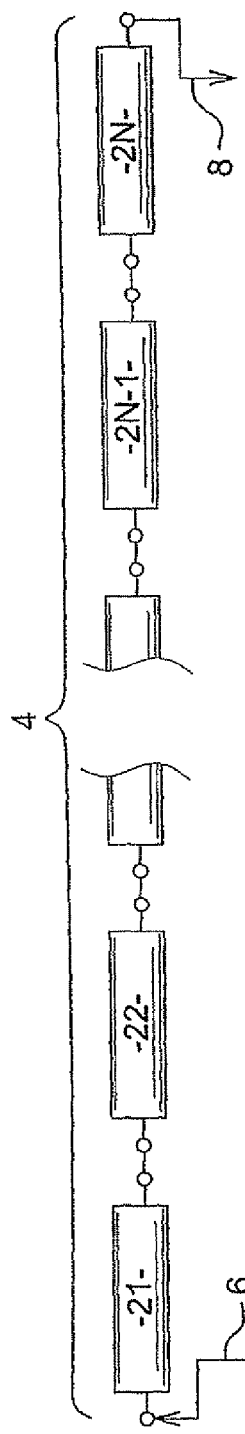
Figure 15:
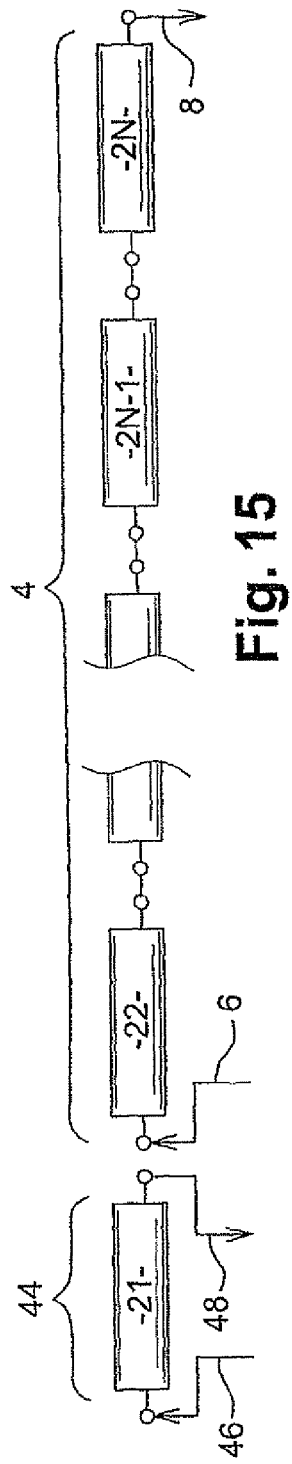
Figure 16:
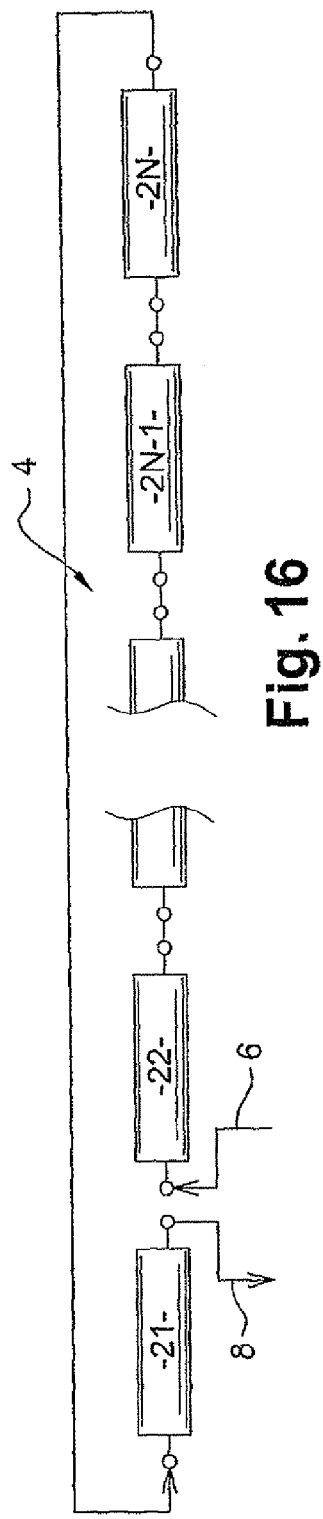

In asynchronous operating mode, it is also possible to envisage that one or more other, or additional, for example desorption, loops will appear and disappear during operation. This is illustrated in FIGS. 14 to 16. The mixture-injection point 10 is not described, but for this reference is made to the preceding figures.

FIG. 14 corresponds to FIG. 4. The separation loop 4 comprises N columns in series, the columns have an outlet contiguous with the inlet of a following column. The outlet of one column can be connected to the inlet of a following column, with the exception of the outlet of column N which is not connected to the inlet of column 21 such that the separation loop 4 is open. At the inlet of separation loop 4, the eluent-injection point 6 is at the inlet of column 21. At the outlet of loop 4, the fraction draw-off point 8 is at the outlet of column 2N.

In FIG. 15, at the start of a period, the injection point 6 of the separation loop 4 is shifted before the draw-off point 8 of the separation loop 4. The eluent-injection point 6 of the separation loop 4 is shifted by at least one column towards the draw-off point 8 of the separation loop, in the direction of flow of the mixture to be separated in the columns, at least one column remaining between the injection point 6 and the draw-off point 8. The shifting is for example by one column. The shifting in the direction of flow places the injection point 6 at the inlet of column 22. The column 21 is shifted out of the separation loop 4.

By shifted column is meant a column which appears during the shifting, between the draw-off point 8 and the injection point 6 of the separation loop 4, in the direction of flow. A shifted column is therefore a column excluded from a loop, for example from the separation loop 4 during the shifting of the injection point 6 of the separation loop 4. A shifted column does not necessarily have its inlet and outlet contiguous with the outlet and inlet respectively of the separation loop 4. Indeed, a shifted column can appear when another, for example desorption, loop is already contiguous with the separation loop 4; the shifted column then appears between the two loops, for example in the direction of flow between the desorption loop and the separation loop 4.

In FIG. 15 once again, during a period, an additional or desorption loop 44 appears for the shifted column 21. This desorption loop 44 which has appeared has the same characteristics as the desorption loop described previously, namely an open structure and eluent-injection point at the inlet and fraction draw-off point at the outlet. Thus the device of FIG. 15 comprises a separation loop 4 of N-1 columns and a desorption loop 44 of one column. Several fractions are collected from the device, at least one fraction being able to be collected at the outlet of each zone.

In FIG. 16, at the end of the period, the draw-off point 8 of the separation loop 4 is in turn shifted by as many columns as the number by which the injection point 6 of the separation loop 4 has been shifted. For example, for a shifting by one column, the injection point 6 is shifted by one column; the desorption loop 44 is then removed. Thus the device of FIG. 16 comprises a separation loop 4 of N columns. The configuration of FIG. 16 is the same as the configuration of FIG. 5. The opening of the separation loop 4 has been shifted by one column.

The appearance then the removal of a desorption loop during a period can be repeated over as many periods as there are columns in the separation loop 4; at the end of the last period, the device has operated over a cycle and returned to the configuration of the positions of the injection 6 and draw-off 8 points of FIG. 14. It could also be considered that in FIGS. 14 and 16, the desorption zone comprises zero columns and that the injection 46 and draw-off 48 points of the desorption loop 44 are merged.

This latter operation described is also useful for devices comprising a small number of columns, for example two columns.

It is also possible to envisage in FIGS. 14 to 16 that the number of shifted columns is greater than one single shifted column. A desorption loop appearing could then comprise more than one column. Also, it is possible to create several desorption loops from several shifted columns.

Also, it is possible to envisage types of zones other than desorption zones. Alternatively to or cumulatively with one or more desorption loops, it is possible to provide, for example, column washing and/or stationary phase regeneration zones, the washing and/or regeneration being able to be carried out by reversing the direction of flow of the chromatographic fluid. What has been described previously is applicable to these other types of loops. These other loops are open. These loops also comprise an injection point at the inlet and a draw-off point at the outlet. For example, a stationary phase in the form of ion-exchange resin can be regenerated by a regeneration loop comprising at the inlet a regeneration solution injection point and at the outlet the collection of what has been eluted.

The device and the method described can also operate according to a mode which is both synchronous and asynchronous over one cycle or according to a synchronous mode over one cycle and asynchronous mode over another cycle. Thus, it is possible to adapt the operation of the device and method according to FIGS. 8 to 10, 11 to 13 and 14 to 16 to the operation of the device and method according to FIGS. 4 to 7. The advantage is that the desorption and/or regeneration loops can be constituted by an average number of columns which can be finely adjusted over the period, a number which is an integer (synchronous operation) or non-integer (asynchronous operation).

Also, it is possible to envisage that the device comprises more than one separation loop, for example at least two contiguous separation loops. These separation loops can be alternated with one or more desorption-type or other loops. The various operations described also apply to this embodiment.

In the above, each loop can be eluted with eluents of a different kind or of different compositions. This makes it possible to:

modify the eluting power, for example by changing the polarity, the pressure, the temperature, the pH, the ionic strength;

regenerate the phase;

use an eluent containing a displacer (preferentially the most-retained product at a high concentration of the order of magnitude of the concentration of feedstock) in the separation loop.

Also, the device can comprise only external pumps for the injection of the feedstock and/or the eluent(s). But the device can moreover comprise a pump inserted between at least two of the columns of the device; this makes it possible to divide the pressure gradient which becomes established in the columns of the device. Also, the device can comprise a pump between each column, which makes it possible to exploit each of the columns at its optimum pressure.

In a general manner, the process described is a "non-SMB" process.

The device 1 described can in particular operate with a control suitable for shifting by at least one column the positions of the injection and draw-off points. This shifting by the control can be simultaneous in manner or occur at different times. It is also possible to envisage an operation with a shifting which is simultaneous or occurs at different times.

In a general fashion, for the devices and processes of FIGS. 8 to 16 where several draw-off points are provided, it is possible to envisage that different fractions are collected according to the draw-off points. For example a fraction F4 is collected at the point 48 while the fractions F3 then F2 are collected at the point 8, then a fraction F3 is collected at the point 48 and fractions F2 then F1 are collected at the point 8. Each draw-off point can have a program for collection at the time appropriate to it.

The process described applies to the purification of compounds which can be separated by chromatographic processes, for example:
- the purification of synthetic molecules for fine chemicals: for example the separation of optical isomers in particular for pharmacy;
- the separation or the purification of sugars in particular for the agri-food industry;
- the separation or purification of bio-molecules for example: peptides, proteins, monoclonal antibodies, oligo-nucleotides, oligo-saccharides;
- the separation or purification of compounds originating from the petrochemical industry.

Embodiment examples are given in relation to FIGS. 17 to 26. In these figures, the x-axes indicate the column number, the y-axes indicating the concentration of compounds in g/l. The bold, dotted curve indicates the raffinate curve, the other curve indicating the extract.

EXAMPLE 1

This process has also been validated by simulation for the purification of 1,2,3,4-tetra-1-hydronaphthol on a chiralpak AD 20 μm phase using an eluent of composition n-heptane/2-propanol/trifluoroacetic acid 95/5/0.2 (v/v/v). The publication by Ludemann, Nicoud and Bailly in Separation Science and Technology, 35(12), pp 1829-1862, 2000 gives all the parameters necessary for simulation of the process.

The variables used for the simulation are:
- 2 columns with an internal diameter of 1 cm and length of 10 cm;
- The temperature is 25° C.;
- Eluent flow rate of 22 mL/min, except when the feedstock is injected, the eluent flow rate is then zero;
- A feedstock composed of the racemic mixture dissolved in the eluent at a total concentration of 20 g/L, this feedstock is injected at a flow rate of 4 mL/min over 0.1 minute;
- The period used is 0.98 minutes, the duration of the cycle is two periods i.e. 1.96 minutes.

By simulating the following sequence, repeated in a cyclical fashion, with reference to FIGS. 1 and 2:

| Time interval in the cycle (minute) | Position of the eluent line | Position of the feedstock line | Collection of the extract | Collection of the raffinate |
|---|---|---|---|---|
| 0.00 to 0.44 | 211 | | 222 | |
| 0.44 to 0.54 | 211 | 221 | 222 | |
| 0.54 to 0.59 | 211 | | 222 | |
| 0.59 to 0.98 | 211 | | | 222 |
| 0.98 to 1.42 | 221 | | 212 | |
| 1.42 to 1.52 | 221 | 211 | 212 | |
| 1.52 to 1.57 | 221 | | 212 | |
| 1.57 to 1.96 | 221 | | | 212 |

The calculated purities are greater than 98% for each of the two collections.

FIGS. 17 to 21 show the development of the internal concentration profile simulated over a period according to the assembly illustrated in FIG. 1 after a sufficient operating period making it possible to attain a steady operating regime.

Figure 17:
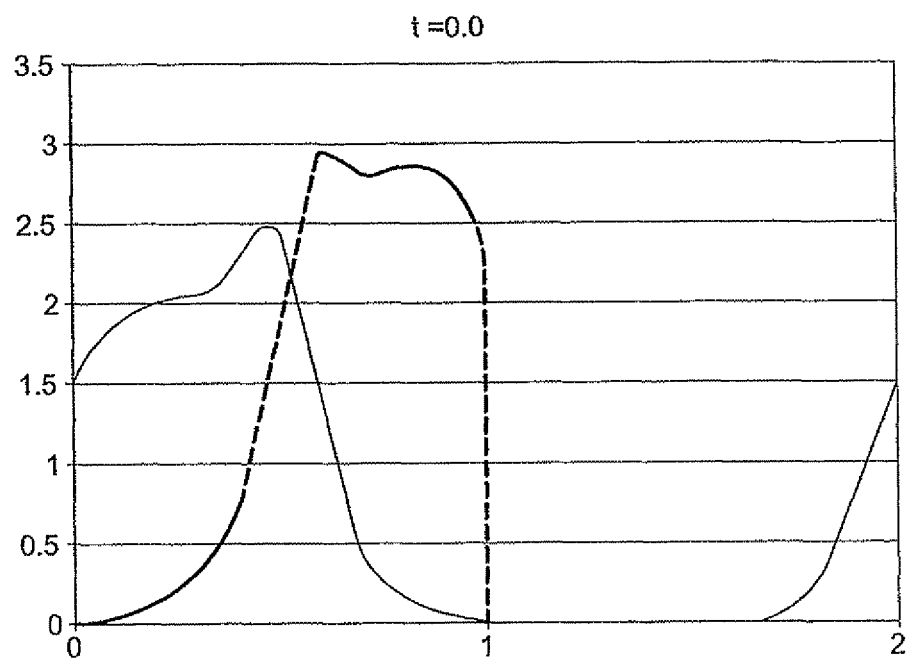
FIGS. 17 to 26, examples of elution graphs of compounds.

FIG. 17 shows the internal concentration profile at time t=0.00 i.e. the start of collection of the extract.

Figure 18:
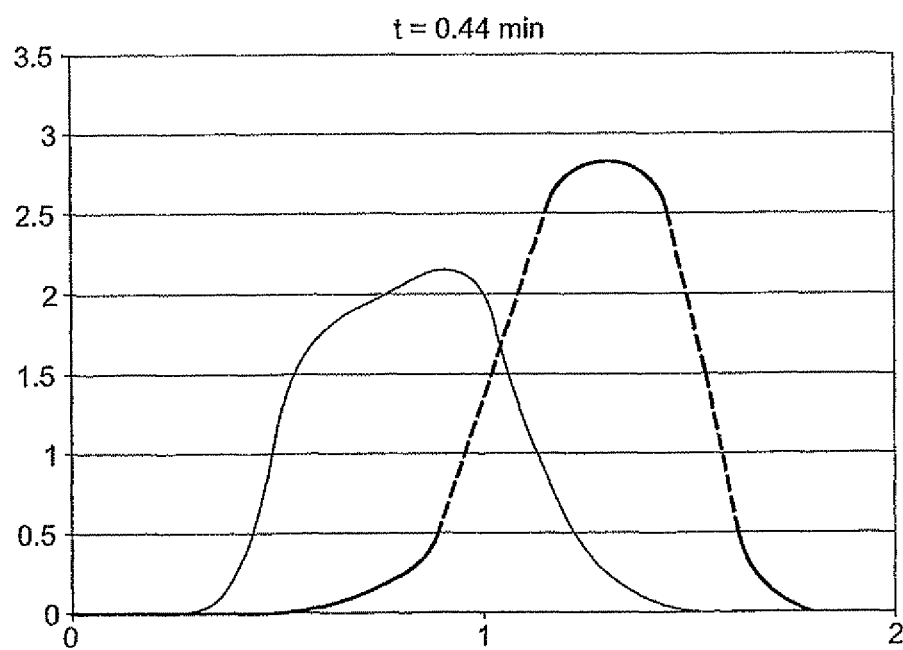
Figure 19:
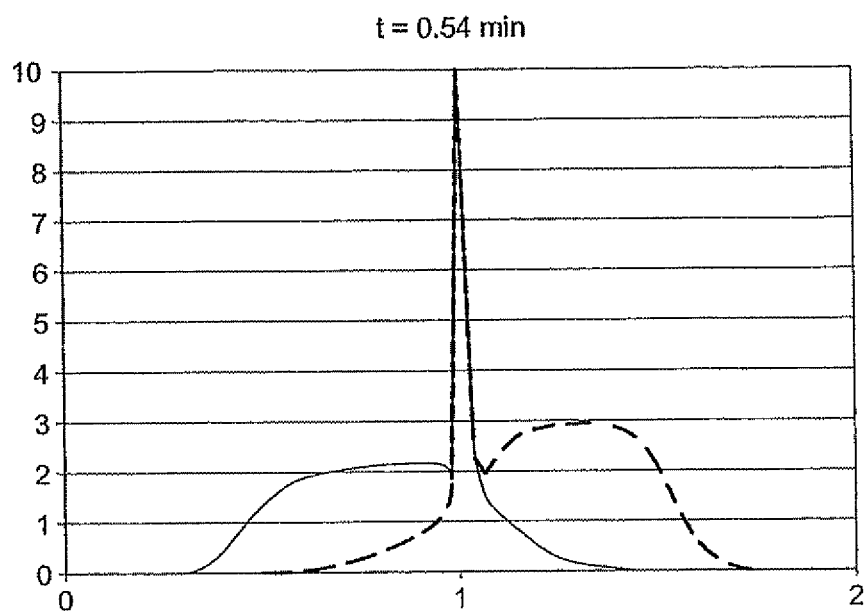

FIGS. 18 and 19 show the internal concentration profiles at time t=0.44 minute and 0.54 minute respectively at the start and the end of the injection.

Figure 20:
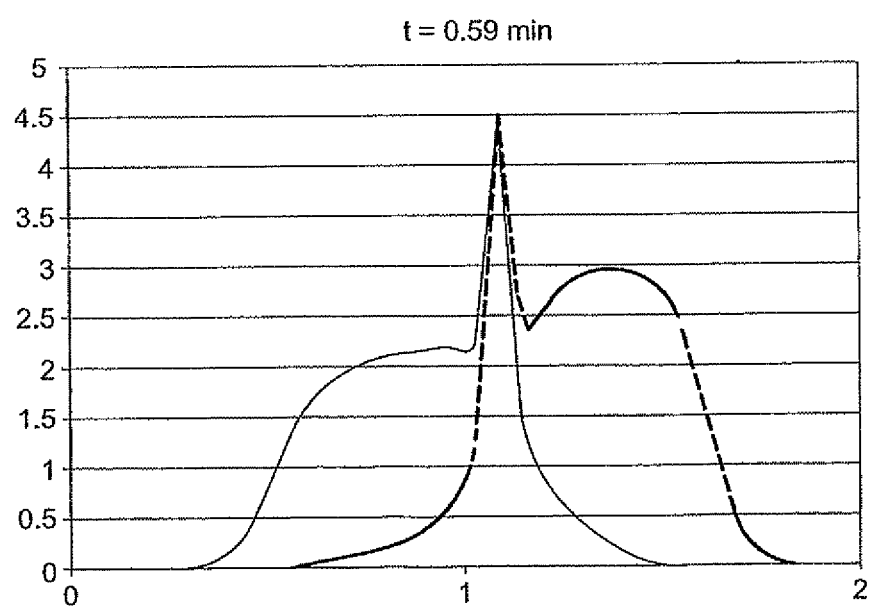

FIG. 20 shows the internal concentration profile at time t=0.59 minute i.e. the end of collection of the extract and the start of the collection of the raffinate.

Figure 21:
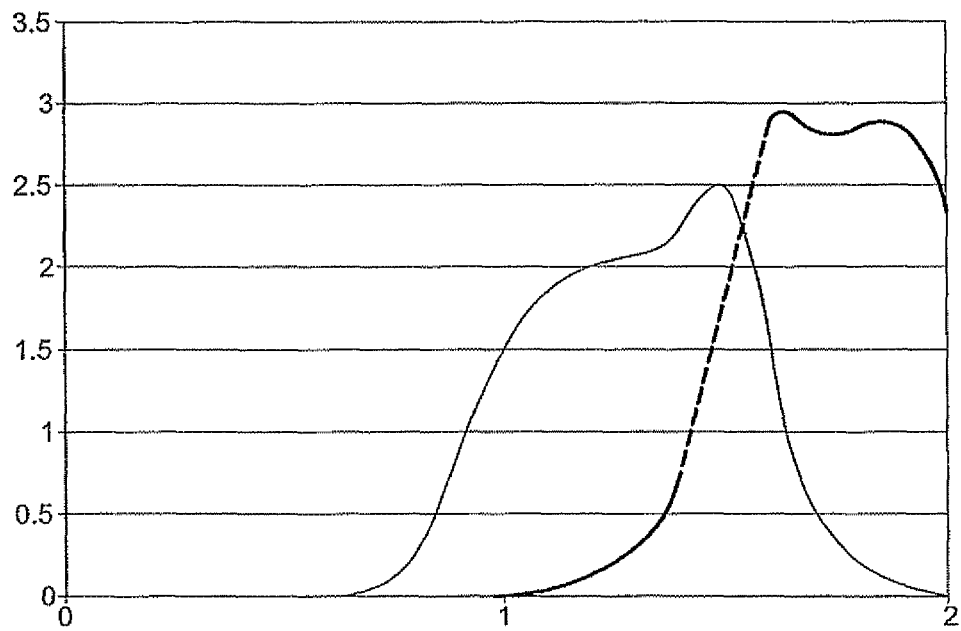

FIG. 21 shows the internal concentration profile at time t=0.98 minute i.e. the end of collection of raffinate.

At time t=0.98 minute the eluent-injection point and the collection point are shifted, as indicated in the table above.

In FIGS. 17 and 21 it is clearly apparent that the internal concentration profiles are spread over broadly more than one column unlike the two-column cyclojet process which by construction means that one of the two columns is always filled with eluent. The present method and device are less expensive.

EXAMPLE 2

By adopting the conditions of Example 1 over three columns the cycle time is equal to 2.94 minutes i.e. three periods, using the following sequencing, repeated in a cyclical fashion:

(the columns are numbered 21, 22, 23, with 211 and 212, 221 and 222, 231 and 232 respectively for inlet and outlet)

| Time interval in the cycle (minute) | Position of the eluent line | Position of the feedstock line | Collection of the extract | Collection of the raffinate |
|---|---|---|---|---|
| 0 to 0.59 | 211 | | 232 | |
| 0.59 to 0.78 | 211 | | | 232 |
| 0.78 to 0.88 | 211 | 231 | | 232 |
| 0.88 to 0.98 | 211 | | | 232 |
| 0.98 to 1.57 | 221 | | 212 | |
| 1.57 to 1.76 | 221 | | | 212 |
| 1.76 to 1.86 | 221 | 211 | | 212 |
| 1.86 to 1.96 | 221 | | | 212 |
| 1.96 to 2.55 | 231 | | 222 | |
| 2.55 to 2.74 | 231 | | | 222 |
| 2.74 to 2.84 | 231 | 221 | | 222 |
| 2.84 to 2.94 | 231 | | | 222 |

The purities calculated are greater than 99.5% for each of the two collections.

FIGS. 22 to 25 show the development of the internal concentration profile simulated over a period after a sufficient operating time making it possible to attain a steady operating regime.

Figure 22:
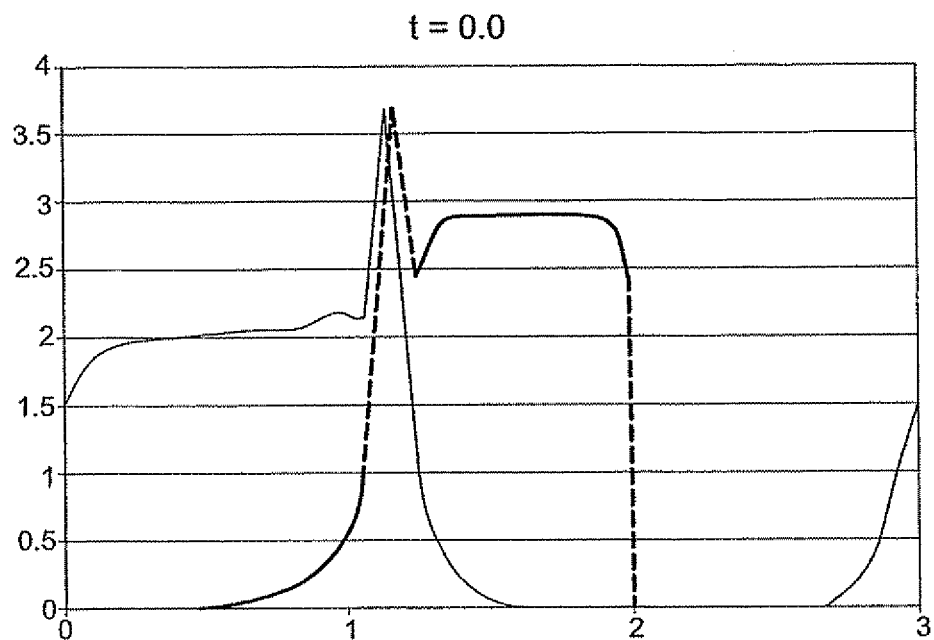

FIG. 22 shows the internal concentration profile at time t=0.00 minute i.e. the start of collection of the extract.

Figure 23:
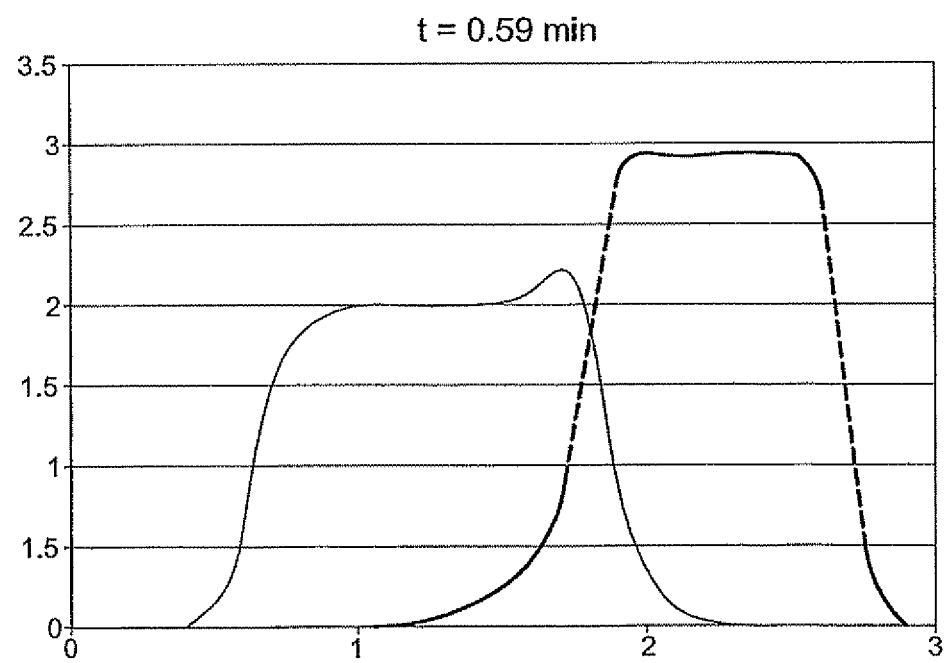

FIG. 23 shows the internal concentration profile at time t=0.59 minute i.e. the end of collection of the extract and the start of collection of the raffinate.

Figure 24:
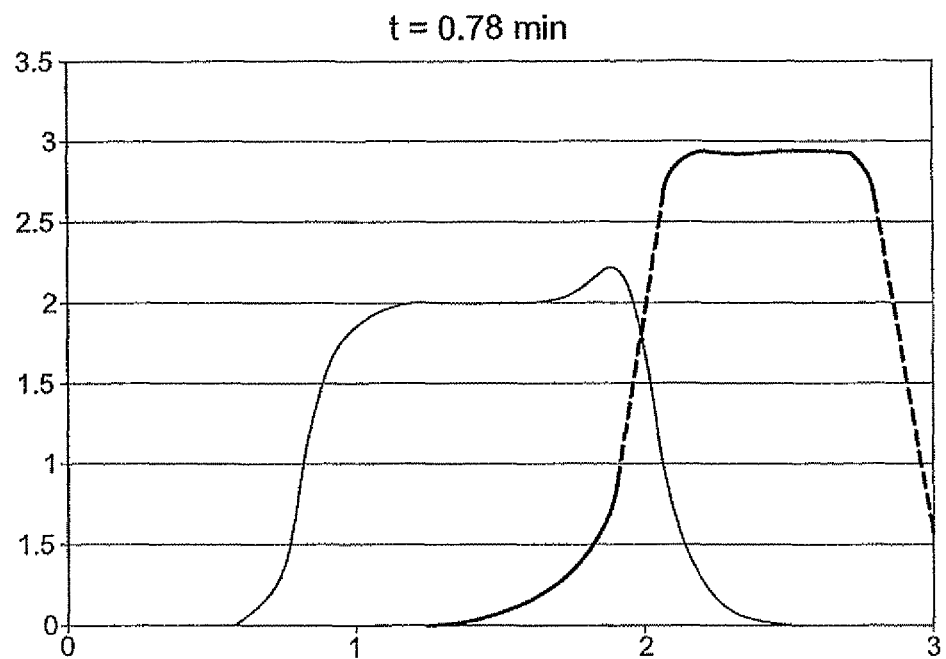
Figure 25:
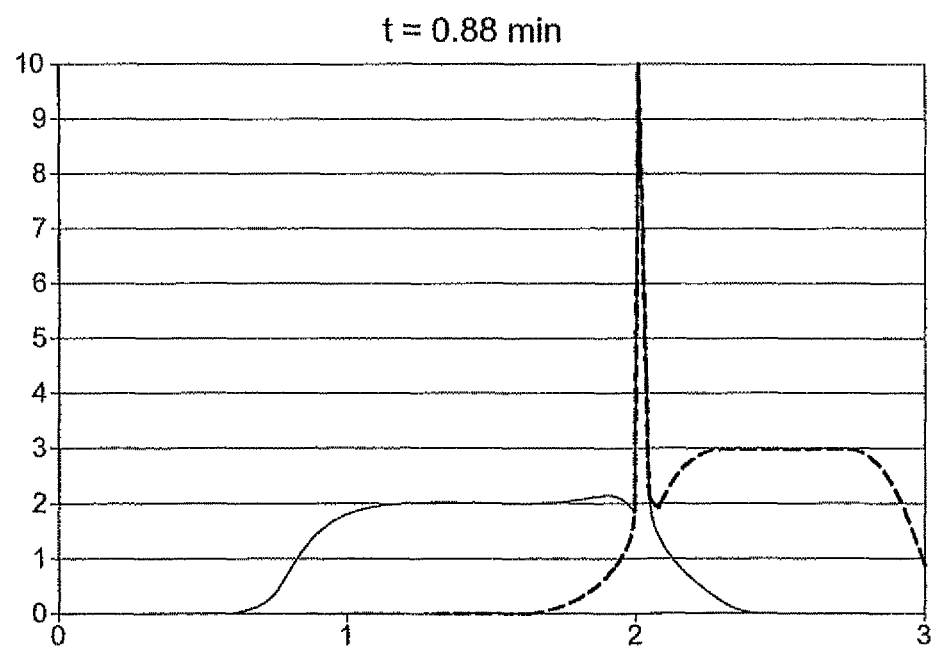

FIGS. 24 and 25 show the internal concentration profile at time t=0.78 minute and 0.88 minute i.e. the time of the start and end of injection of the feedstock.

Figure 26:
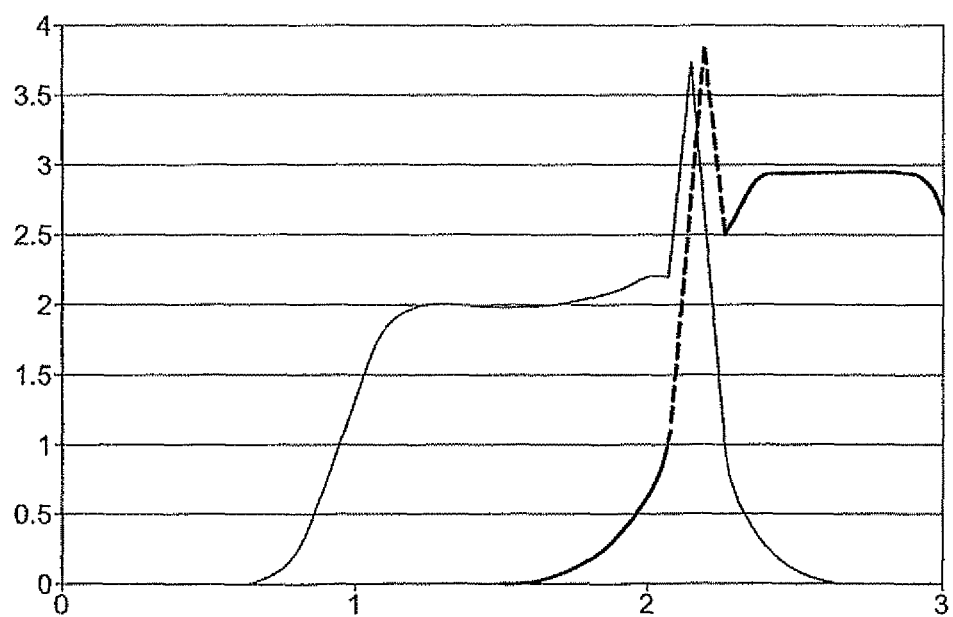

FIG. 26 shows the internal concentration profile at time t=0.98 minute i.e. the end of collection of the raffinate.

At time t=0.98 minute the eluent-injection point and the collection point are shifted, as indicated in the table above.

FIGS. 22 to 25 show that the internal concentration profiles are spread over a large part of the separation loop. With reference to FIGS. 17 to 25, it appears that this method makes it possible to exploit a large part of the columns used in the separation loop. Thus, in Example 1, two columns constituted the separation zone and the internal concentration profiles constantly occupied between 1.25 and 1.5 columns whereas in Example 2, three columns constituted the separation zone and the internal concentration profiles constantly occupied between 2.25 and 2.5 columns.

EXAMPLE 3

This process was tested experimentally on a three-column device. The columns with an internal diameter of 2.6 cm were filled to a height of 11.2 cm on average with 25 μm Kromasil C18 reversed-phase. The eluent used is a 3.81 g/L Na2B4O7, 10H2O buffer in water mixed with ethanol in respective volume proportions of 70/30 at 22° C. The mixture to be treated is obtained by diluting 1 g of Patent blue and 1 g of azorubine (red product) in the eluent. The feedstock thus prepared is dark violet in color.

The flow rate of the first eluent line is 20 mL/min, the flow rate of the first eluent line is zero when the feedstock is injected. The flow rate of the second eluent line is equal to 20 mL/min, when the system is in a shifted-column situation and zero if not.

The columns are numbered 21, 22, 23, with 211 and 212, 221 and 222, 231 and 232 for inlet and outlet respectively.

The sequencing established for each cycle is:

| Time interval in the cycle (minute) | Position of the eluent line 2 | Collection of blue outlet 2 | Position of eluent line 1 | Position of the feedstock line | Collection of blue outlet 1 | Collection of red outlet 1 |
|---|---|---|---|---|---|---|
| 0.00 to 0.08 | 211 | 212 | 221 | 231 | | 232 |
| 0.08 to 0.94 | 211 | 212 | 221 | | | 232 |
| 0.94 to 1.82 | | | 221 | | 212 | |
| 1.82 to 1.89 | | | 221 | 211 | 212 | |
| 1.89 to 1.97 | 221 | 222 | 231 | 211 | | 212 |
| 1.97 to 2.83 | 221 | 222 | 231 | | | 212 |
| 2.83 to 3.71 | | | 231 | | 222 | |
| 3.71 to 3.78 | | | 231 | 221 | 222 | |
| 3.78 to 3.86 | 231 | 232 | 211 | 221 | | 222 |
| 3.86 to 4.72 | 231 | 232 | 211 | | | 222 |
| 4.72 to 5.60 | | | 211 | | 232 | |
| 5.60 to 5.67 | | | 211 | 231 | 232 | |

At the end of a few cycles, a blue collection and a red collection are obtained, a visible sign of a significant separation of the two products.

What is claimed is:

1. A method for separating fractions of a mixture to be separated, in a device (1) having:
    several chromatography columns (21, 22, 23, etc.) mounted in series,
    a single separation zone constituted by a constantly open separation loop comprising, at the inlet of the open separation loop an eluent-injection point (6) for injecting eluent into one of the columns and, at the outlet of the open separation loop, a draw-off point (8) for withdrawal of a fraction of the mixture, with no other fluid circulating between the inlet and the outlet of the open separation loop, the method comprising:
    a mixture injection stage for discontinuous injection of the mixture to be separated into the open separation loop (4),
    a collection stage for collection of at least two fractions, and
    a shifting stage for shifting by at least one column the eluent-injection point (6) and the fraction draw-off point (8) of the separation loop (4),
    wherein
    (a) during the shifting stage, the eluent-injection and draw-off points of the separation loop are shifted at different times, or
    (b) said device further comprises at least one other loop, or
    (c) in which the eluent-injection and draw-off points of the separation loop are not contiguous.

2. The method according to claim 1, in which the mixture injection stage is carried out independently of the collection and shifting stages.

3. The method according to claim 1, in which the mixture is injected at the inlet of a column which is different from the column where the eluent is injected.

4. The method according to claim 1, in which the mixture is injected into the separation loop, at a point distant from the eluent-injection and collection points of at least one column.

5. The method according to claim 1, in which the shifting of the eluent-injection and collection points is carried out in the direction of flow of the mixture to be separated in the columns.

6. The method according to claim 1, in which at least two fractions are collected successively at the collection point of the separation loop.

7. The method according to claim 1, wherein the device comprising two columns in series,
    the inlet of the separation loop being at the inlet of one of the columns and
    the outlet of the separation loop being at the outlet of the other column, the collection stage comprising the collection of two fractions at the draw-off point at the outlet of the separation loop, one of the fractions, the extract, being more retained in the columns than the other fraction, the raffinate, which is less retained in the columns.

8. The method according to claim 1, in which, during the shifting stage, the eluent-injection and draw-off points of the separation loop are shifted at different times.

9. The method according to claim 8, in which, during the shifting stage,
    the eluent-injection point of the separation loop is shifted by at least one column towards the draw-off point of the separation loop, in the direction of flow of the mixture to be separated in the columns, at least one column remaining between the injection point and the draw-off point.

10. The method according to claim 9, in which, during the shifting stage,
the draw-off point of the separation loop is shifted in the direction of flow of the mixture to be separated in the columns, by as many columns as the number by which the eluent-injection point of the separation loop has been shifted.

11. The method according to claim 9, the device also comprising:
at least one other loop, every other loop being open and comprising at the inlet another eluent-injection point and at the outlet another collection point, the method comprising, after shifting the eluent-injection point of the separation loop by at least one column,
the shifting by at least one column of the draw-off point of one of the other loops.

12. The method according to claim 11, in which each loop is eluted with eluents of a different kind or of different compositions.

13. The method according to claim 9, in which, after the shifting of the eluent-injection point of the separation loop by at least one column,
at least one other loop appears with at least one shifted column, every other loop having appeared being open and comprising at the inlet another injection point and at the outlet another draw-off point.

14. The method according to claim 8, in which each loop other than the separation loop (4) ensures the desorption of the most-retained fractions of mixture in the columns or the regeneration of the columns.

15. The method according to claim 1, in which, during the shifting stage,
the eluent-injection and draw-off points of the separation loop are shifted simultaneously.

16. The method according to claim 15, wherein
said device comprises at least one other loop, every other loop being open and comprising at the inlet another eluent-injection point and at the outlet another draw-off point, and
the collection stage also comprising collection at the draw-off point of every other loop.

17. The method according to claim 16, in which each loop is eluted with eluents of a different kind or of different compositions.

18. The method according to claim 16, in which, during the shifting stage of the eluent-injection and collection points of the separation loop,
the other eluent-injection and collection points of every other loop are shifted simultaneously with the eluent-injection and collection points of the separation loop.

19. The method according to claim 1, in which the eluent-injection and draw-off points of the separation loop are contiguous.

20. The method according to claim 1, in which the eluent-injection and draw-off points of the separation loop are not contiguous.

21. The method according to claim 20, in which the eluent-injection and draw-off points are separated by at least one other separation loop.

22. The method according to claim 1, in which the injection is only carried out during certain periods.

23. The method according to claim 1, the method being cyclical.

24. The method according to claim 1 according to which the eluent used is a single-phase fluid constituted by at least one gaseous product at ambient pressure and temperature.

25. The method according to claim 1 according to which the eluent used is a fluid containing at least carbon dioxide in the supercritical state.

26. The method according to claim 1 according to which the eluent used is a homogeneous fluid containing at least carbon dioxide.

27. The method according to claim 1, in which the eluent is recycled by means chosen from the group consisting of distillation, evaporation and the use of membranes.

28. The method according to claim 1, wherein said device further comprises at least one desorption loop comprising, at the inlet of the desorption loop, an injection point (46) for injection of eluent into a column of the desorption loop, and, at the outlet of the desorption loop, a draw-off point (48) for withdrawing a fraction of the mixture, and
wherein said method further comprises shifting by at least one column the eluent injection point (46) and the fraction draw-off point (48) of said at least one desorption loop,
wherein the eluents at the inlet of the separation loop and the inlet of said at least one desorption loop have different compositions.

29. A method for separating fractions of a mixture to be separated, in a device (1) having:
several chromatography columns (21, 22, 23, etc.) mounted in series,
a single separation zone constituted by a constantly open separation loop comprising, at the inlet of the open separation loop an eluent-injection point (6) for injecting eluent into one of the columns and, at the outlet of the open separation loop, a draw-off point (8) for withdrawal of a fraction of the mixture, the method comprising:
a mixture injection stage for discontinuous injection of the mixture to be separated into the open separation loop (4),
a collection stage for collection of at least two fractions, and
a shifting stage for shifting by at least one column the eluent-injection point (6) and the fraction draw-off point (8) of the separation loop (4);
wherein said device further comprises at least one desorption loop comprising, at the inlet of the desorption loop, an injection point (46) for injection of eluent into a column of the desorption loop, and, at the outlet of the desorption loop, a draw-off point (48) for withdrawing a fraction of the mixture, and
wherein the eluents at the inlet of the separation loop and the inlet of said at least one desorption loop have different compositions.

30. A method for separating fractions of a mixture to be separated, in a device (1) having:
several chromatography columns (21, 22, 23, etc.) mounted in series,
a single separation zone constituted by a constantly open separation loop comprising, at the inlet of the open separation loop an eluent-injection point (6) for injecting eluent that is recycled by chosen from the group consisting of distillation, evaporation and the use of membranes into one of the columns and, at the outlet of the open separation loop, a draw-off point (8) for withdrawal of a fraction of the mixture, the method comprising:
a mixture injection stage for discontinuous injection of the mixture to be separated into the open separation loop (4),
a collection stage for collection of at least two fractions,
a shifting stage for shifting by at least one column the eluent-injection point (6) and the fraction draw-off point (8) of the separation loop (4).

* * * * *